(12) United States Patent
Sahade

(10) Patent No.: US 7,862,867 B2
(45) Date of Patent: Jan. 4, 2011

(54) BIFUNCTIONAL POLYMERIZABLE COMPOUND, POLYMERIZABLE LIQUID CRYSTAL COMPOSITION, AND ORIENTED FILM

(75) Inventor: Daniel Antonio Sahade, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 83 days.

(21) Appl. No.: 12/444,338

(22) PCT Filed: Oct. 2, 2007

(86) PCT No.: PCT/JP2007/069250
§ 371 (c)(1),
(2), (4) Date: Apr. 3, 2009

(87) PCT Pub. No.: WO2008/044536
PCT Pub. Date: Apr. 17, 2008

(65) Prior Publication Data
US 2010/0044632 A1 Feb. 25, 2010

(30) Foreign Application Priority Data
Oct. 5, 2006 (JP) .............................. 2006-273609

(51) Int. Cl.
C09K 19/34 (2006.01)
C09K 19/38 (2006.01)
C09K 19/12 (2006.01)
C07D 307/58 (2006.01)
C08F 24/00 (2006.01)
G02B 5/30 (2006.01)

(52) U.S. Cl. .............. 428/1.1; 252/299.61; 252/299.66; 549/320; 549/323; 526/269; 526/270

(58) Field of Classification Search .................. 428/1.1; 252/299.61, 299.66, 299.67; 549/320, 323; 527/269, 270
See application file for complete search history.

(56) References Cited

U.S. PATENT DOCUMENTS

| | | | | |
|---|---|---|---|---|
| 4,909,957 A | * | 3/1990 | Sakaguchi et al. ..... | 252/299.61 |
| 5,026,506 A | * | 6/1991 | Koden et al. ........... | 252/299.61 |
| 5,256,330 A | * | 10/1993 | Koyama et al. ........ | 252/299.61 |
| 5,308,540 A | * | 5/1994 | Sakaguchi et al. ..... | 252/299.61 |
| 5,849,217 A | * | 12/1998 | Nakamura et al. ..... | 252/299.61 |
| 2007/0108410 A1 | * | 5/2007 | Goto et al. ............. | 252/299.61 |
| 2009/0088545 A1 | * | 4/2009 | Sahade et al. ............... | 526/270 |

FOREIGN PATENT DOCUMENTS

| | | |
|---|---|---|
| JP | 62-70407 A | 3/1987 |
| JP | 9-208957 A | 8/1997 |
| JP | 2004-262884 A | 9/2004 |
| JP | 2005-330462 A | 12/2005 |
| WO | WO-2006/115112 A1 | 11/2006 |

OTHER PUBLICATIONS

Ramarajan et al., "Organic Syntheses" 1983, vol. 61, pp. 56-59, An Annual Publication of Satisfactory methods for the Preparation of Organic Chemical.

\* cited by examiner

*Primary Examiner*—Shean C Wu
(74) *Attorney, Agent, or Firm*—Birch, Stewart, Kolasch & Birch, LLP

(57) ABSTRACT

Disclosed is a bifunctional polymerizable compound represented by the formula [1]. Also disclosed is a polymerizable liquid crystal composition comprising at least one bifunctional polymerizable compound represented by the formula [1] and a polymerizable liquid crystal compound. The bifunctional polymerizable compound has a high polymerizability. When added to a polymerizable liquid crystal compound to prepare a polymerizable liquid crystal composition, the bifunctional polymerizable compound enables to remarkably improve the thermal stability of a polymer produced from the composition. The polymerizable liquid crystal composition containing the bifunctional polymerizable compound has a low crystallization temperature and shows a stable liquid-crystallinity under ordinary environment

[1]

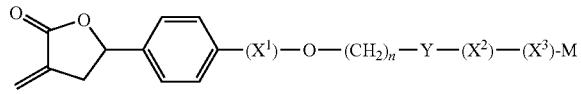

wherein $X^1$, $X^2$ and $X^3$ independently represent a single bond or a benzene ring; Y represents —O— or a single bond; M represents a lactone ring or an acrylate group; and n represents an integer of 4 to 10.

13 Claims, 5 Drawing Sheets

BIFUNCTIONAL POLYMERIZABLE COMPOUND, POLYMERIZABLE LIQUID CRYSTAL COMPOSITION, AND ORIENTED FILM

TECHNICAL FIELD

This invention relates to a bifunctional polymerizable compound, an additive for a polymerizable composition, a polymerizable composition and a polymerizable liquid crystal composition, and also to a polymer and oriented film obtainable from the composition.

BACKGROUND ART

From requirements for display quality improvements, weight reductions and the like in liquid crystal displays, there is an increasing demand for polymer films with controlled internal molecular orientation structures as optical compensation films such as polarizer plates and retarder plates. With a view to meeting this demand, developments have been made on films making use of optical anisotropy which polymerizable liquid crystal compounds are equipped with.

The term "polymerizable liquid crystal compound" as used herein means a liquid crystal compound, which generally has a polymerizable group and a liquid crystal structure part (a structural part having a spacer moiety and a mesogenic moiety), and as this polymerizable group, an acrylic group is widely employed.

Such a polymerizable liquid crystal compound can be formed into a polymer (film) by a process that irradiates radiation such as ultraviolet rays onto the compound in a liquid crystal state to polymerize the same.

Known processes include, for example, a process that holds a specific polymerizable liquid-crystalline compound having an acrylic group between supports and, while maintaining this compound in a liquid crystal state, irradiates radiation to obtain a polymer (see Patent Document 1); and a process that adds a photopolymerization initiator to a mixture of two polymerizable liquid crystal compounds each having an acrylic group or to a composition, which has been obtained by mixing a chiral liquid crystal to the mixture, and irradiating ultraviolet rays to obtain a polymer (see Patent Document 2).

Polymers (films) obtained by the respective processes are mounted in display devices such as monitors and television sets as polarizer plates, retarder plates and/or the like.

In recent years, the in-cell technology which means the built-in incorporation of external members such as a polarizer plate and a retarder plate has drawn attention as an important element technology for the simplification of next-generation LCD fabrication processes.

Compared with oriented films to be arranged externally, oriented films for use in this in-cell technology are required to show high thermal stability to processes such as high-temperature baking such that their optical anisotropy, transparency and the like remain unchanged. No materials are, however, known at present to be excellent enough to meet this requirement.

Patent Document 1: JP-A 62-70407
Patent Document 2: JP-A 9-208957

DISCLOSURE OF THE INVENTION

Problems to be Solved by the Invention

With the foregoing circumstances in view, the present invention has as a first object thereof the provision of a novel bifunctional polymerizable compound, which has high polymerizability by itself and, when added to a polymerizable liquid crystal compound to provide a polymerizable liquid crystal composition, can provide a polymer, which is obtainable from the composition, with significantly-improved thermal stability.

Further, it is a second object to provide a polymerizable liquid crystal composition, which is composed including the bifunctional polymerizable compound and a polymerizable liquid crystal compound, has a low crystallization temperature, and shows stable liquid crystallinity under an ordinary environment.

Furthermore, it is a third object to provide a polymer and a film, which are obtainable from the polymerizable liquid crystal composition.

Means for Solving the Problems

The present inventor has repeated extensive investigations to solve the above-described problem. As a result, it was found that certain specific bifunctional polymerizable compounds, each of which has an α-methylene-γ-butyrolactone moiety and a lactone moiety or acrylate moiety, are excellent by themselves in polymerizability, are superb in the compatibility with polymerizable liquid crystal compounds, and can provide stable liquid crystal compositions when added to polymerizable liquid crystal compounds, and that polymers and films obtainable from the liquid-crystalline compositions have excellent heat resistance in optical anisotropy and transparency, leading to the completion of the present invention.

Described specifically, the present invention provides:

1. A bifunctional polymerizable compound characterized by being represented by the following formula [1]:

[Chemical Formula 1]

[1]

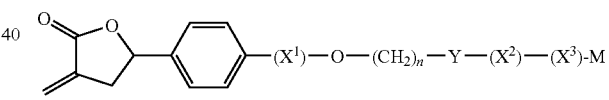

wherein $X^1$, $X^2$ and $X^3$ are each independently a single bond or a benzene ring, Y is —O— or a single bond, M is a lactone ring or an acrylate group, and n stands for an integer of from 4 to 10.

2. The bifunctional polymerizable compound as described above under 1, which is represented by the following formula [1a] or formula [1b]:

[Chemical Formula 2]

[1a]

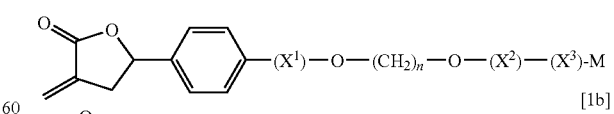

[1b]

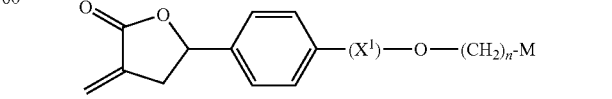

wherein $X^1$, $X^2$, $X^3$, M and n have the same meanings as defined above.

3. The bifunctional polymerizable compound as described above under 1 or 2, wherein M is an organic group represented by the following formula [2] or [3]:

[Chemical Formula 3]

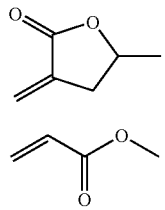

[2]

[3]

4. The additive for a polymerizable composition, comprising a bifunctional polymerizable compound as described above under any one of 1 to 3.

5. The polymerizable composition comprising a bifunctional polymerizable compound as described above under any one of 1 to 3.

6. The polymerizable liquid crystal composition comprising a bifunctional polymerizable compound as described above under 1 and a polymerizable liquid crystal compound.

7. The polymerizable liquid crystal composition as described above under 6, wherein the polymerizable liquid crystal compound has one or two acrylate groups or one lactone ring in a molecule thereof.

8. The polymerizable liquid crystal composition as described above under 6 or 7, wherein the polymerizable liquid crystal compound is a liquid crystal compound represented by the formula [4]:

[Chemical Formula 4]

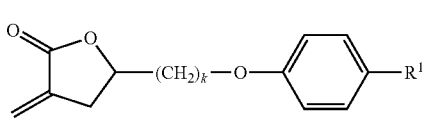

[4]

wherein $X^4$ is a single bond, —COO—, —HC=N— or —C=C—, $X^5$ is a single bond or a benzene ring, $X^6$ is a hydrogen atom, cyano group, methoxy group or fluorine atom, and m stands for an integer of from 2 to 10.

9. The polymerizable liquid crystal composition as described above under 6 or 7, wherein the polymerizable liquid crystal compound is a liquid crystal compound represented by the formula [5]:

[Chemical Formula 5]

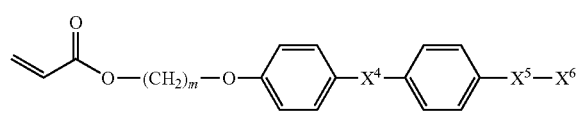

[5]

wherein $R^1$ is an organic group represented by the formula [6] or [7], and k stands for an integer of from 2 to 9,

[Chemical Formula 6]

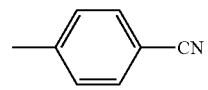

[6]

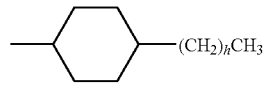

[7]

wherein h stands for an integer of from 4 to 8.

10. The polymerizable liquid crystal composition as described above under 8, further comprising a liquid crystal compound represented by the following formula [5]:

[Chemical Formula 7]

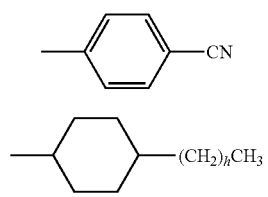

[5]

wherein $R^1$ is an organic group represented by the formula [6] or [7], and k stands for an integer of from 2 to 9,

[Chemical Formula 8]

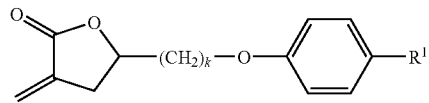

[6]

[7]

wherein h stands for an integer of from 4 to 8.

11. The polymer obtainable from a polymerizable liquid crystal composition as described above under any one of 6 to 10.

12. The oriented film obtainable from a polymerizable liquid crystal composition as described above in any one of 6 to 10.

13. The optical component provided with a polymer as described above under 11 or an oriented film as described above under 12.

Effect of the Invention

The bifunctional polymerizable compound according to the present invention is excellent in the compatibility with a polymerizable liquid crystal compound, and a polymerizable liquid-crystalline composition containing it exhibits stable optical anisotropy. Further, the use of this polymerizable liquid crystalline composition makes it possible to obtain a polymer which is stable in transparency and anisotropy after heating and is extremely good in heat resistance. This polymer is useful as optical anisotropic films such as polarizer plates and retarder plates.

BEST MODE FOR CARRYING OUT THE INVENTION

Figure 1:
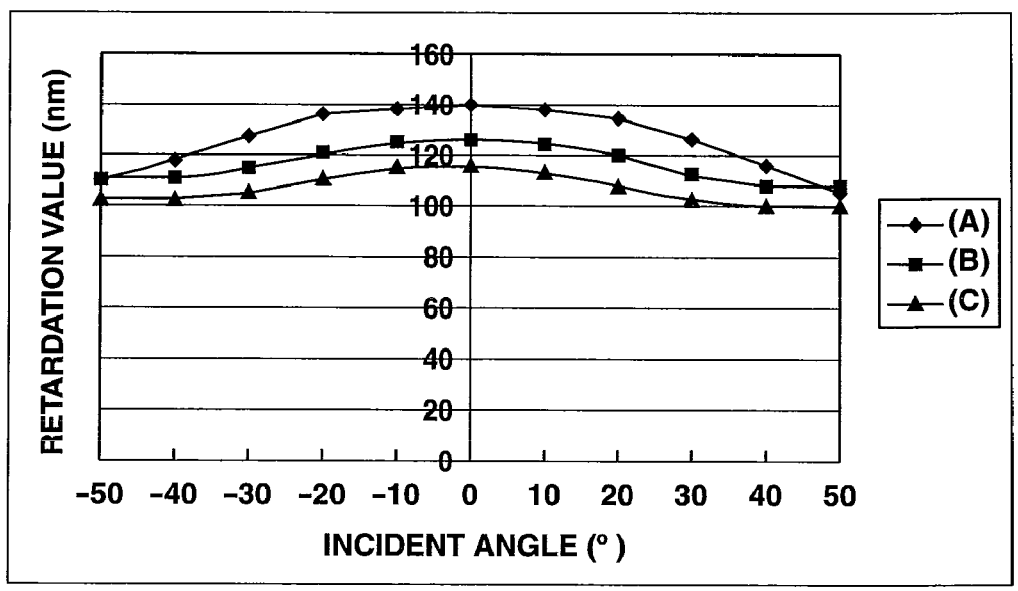
FIG. 1 is a diagram showing (A) the incident-angle-dependency of the retardation value of the film of Example 6 in its unbaked state, (B) the incident-angle-dependent thermal stability of the retardation value of the film after baked at 180° C. for 1 hour, and (C) the incident-angle-dependent thermal stability of the retardation value of the film after baked at 200° C. for 1 hour.
Figure 2:
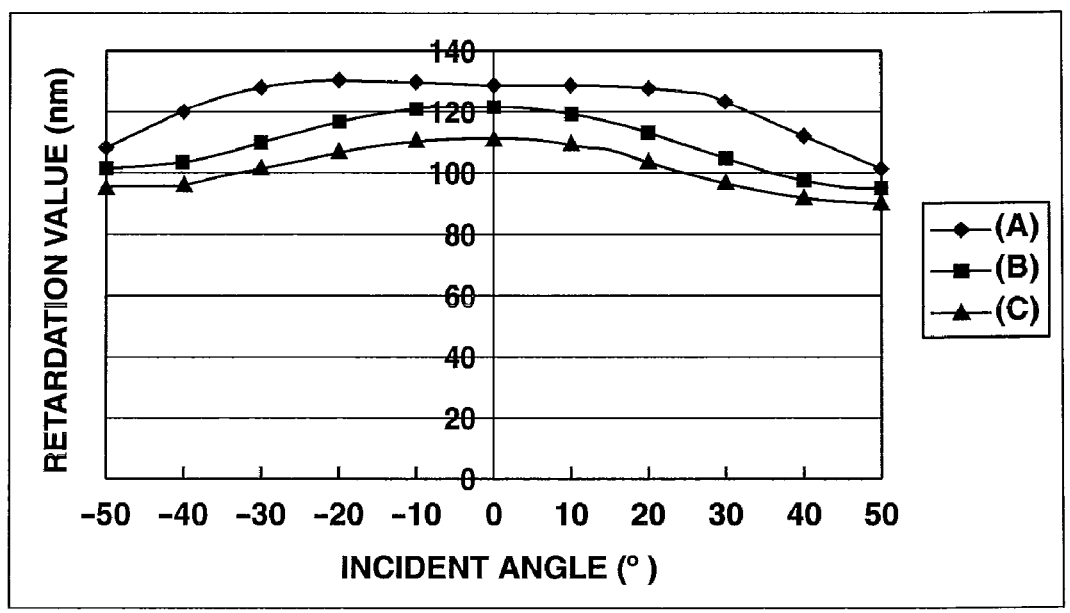
FIG. 2 is a diagram showing (A) the incident-angle-dependency of the retardation value of the film of Example 7 in its unbaked state, (B) the incident-angle-dependent thermal stability of the retardation value of the film after baked at 180° C. for 1 hour, and (C) the incident-angle-dependent thermal stability of the retardation value of the film after baked at 200° C. for 1 hour.
Figure 3:
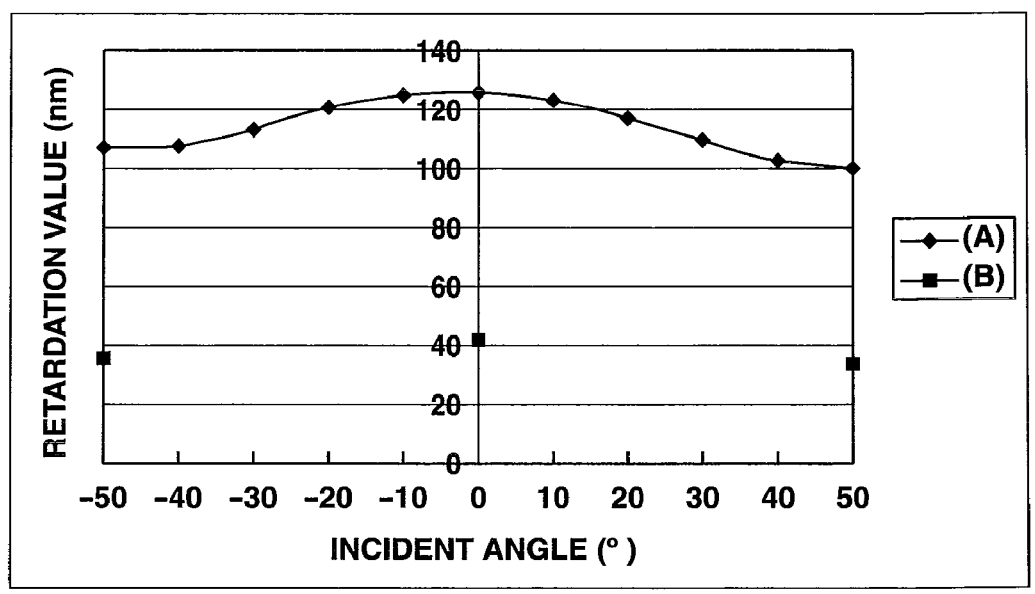
FIG. 3 is a diagram showing (A) the incident-angle-dependency of the retardation value of the film of Comparative Example 1 in its unbaked state, and (B) the incident-angle-dependent thermal stability of the retardation value of the film of Comparative Example 1 after baked at 180° C. for 1 hour.
Figure 4:
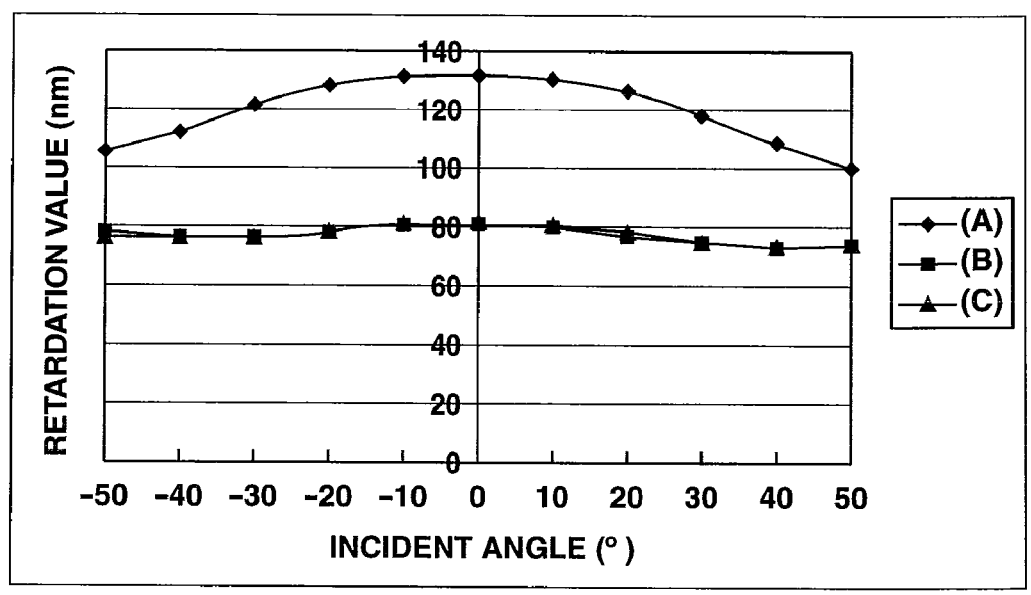
FIG. 4 is a diagram showing (A) the incident-angle-dependency of the retardation value of the film of Comparative Example 2 in its unbaked state, (B) the incident-angle-dependent thermal stability of the retardation value of the film after baked at 180° C. for 1 hour, and (C) the incident-angle-dependent thermal stability of the retardation value of the film after baked at 200° C. for 1 hour.
Figure 5:
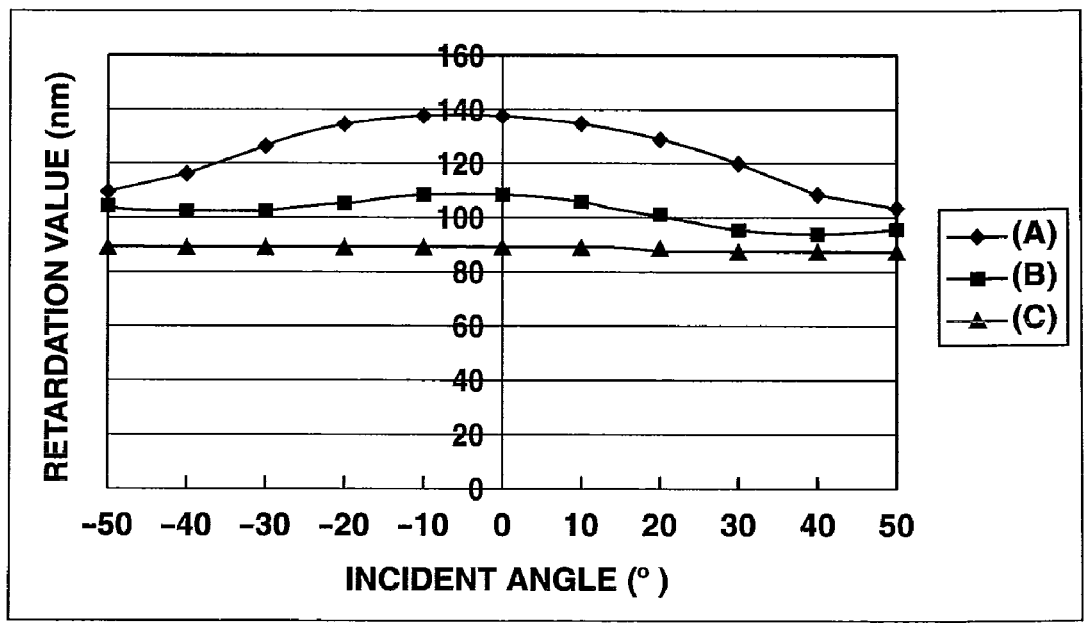
FIG. 5 is a diagram showing (A) the incident-angle-dependency of the retardation value of the film of Comparative Example 3 in its unbaked state, (B) the incident-angle-dependent thermal stability of the retardation value of the film after baked at 180° C. for 1 hour, and (C) the incident-angle-dependent thermal stability of the retardation value of the film after baked at 200° C. for 1 hour.

Certain terms as used herein have the meanings to be described next.

The term "polymerizable liquid crystal compound" means a compound, which has a polymerizable part such as an acrylic group or α-methylenelactone ring and a liquid crystal structure part in its molecule and exhibits a liquid crystal phase. The term "liquid crystal structure" means a structure having a spacer moiety and a mesogenic moiety, which are generally used to indicate a liquid crystal molecule. The term "polymerizable liquid crystal composition" means a composition, which is a mixture containing a polymerizable liquid crystal compound and a bifunctional polymerizable compound and having a property that exhibits a liquid crystalline phase. The term "liquid crystallinity" means to exhibit a liquid crystal phase.

The present invention will hereinafter be described in further detail.

[Bifunctional Polymerizable Compound]

The bifunctional polymerizable compound according to the present invention is represented by the below-described formula [1]. This compound has structures corresponding to a spacer moiety and a mesogenic moiety in a liquid crystal compound, but is a non-liquid crystalline compound which by itself shows no liquid crystallinity.

[Chemical Formula 9]

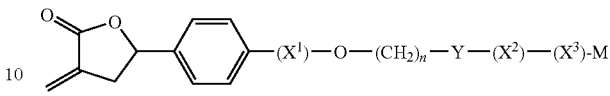

[1]

wherein $X^1$, $X^2$ and $X^3$ are each independently a single bond or a benzene ring, Y is —O— or a single bond, M is a lactone ring or an acrylate group, and n stands for an integer of from 4 to 10.

In the formula [1], the repeating units of methylene group as represented by —$(CH_2)_n$— are a moiety generally called "a spacer moiety," and the repeat number n is an integer of from 4 to 10, preferably an integer of from 4 to 6. It is to be noted that the term "single bond" means that atoms at its opposite ends are directly bonded to each other.

M can be any desired lactone ring, but an α-alkylidene-γ-butyrolactone having a polymerizable group is preferred, with an α-methylene-γ-butyrolactone ring being most suited as it does not give much influence by steric hindrance and has high polymerizability.

As has been described above, the bifunctional polymerizable compound according to the present invention has at least one α-methylene-γ-butyrolactone ring, and this α-methylene-γ-butyrolactone structure is an extremely effective partial structure for imparting high Tg and heat resistance to a polymer to be obtained using the compound.

The bifunctional polymerizable compound according to the present invention, which can afford a polymer having such properties, can be suitably used as an additive for polymerizable compositions prepared with various polymerizable compounds contained therein, and therefore, polymers obtained by polymerizing these compositions are provided with good heat resistance.

In particular, a bifunctional polymerizable compound represented by the following formula [1a] or [1b] is suited in the present invention.

[Chemical Formula 10]

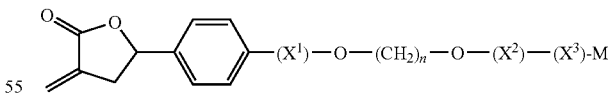

[1a]

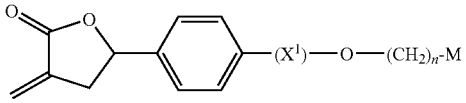

[1b]

wherein $X^1$, $X^2$, $X^3$, M and n have the same meanings as defined above.

Specific examples of the bifunctional polymerizable compound according to the present invention include, but are not limited to, the following compounds (1) to (35).

[Chemical Formula 11]
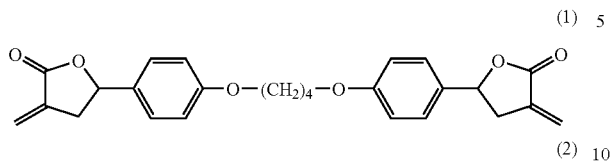 (1)
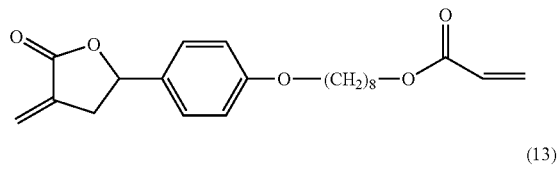 (12)
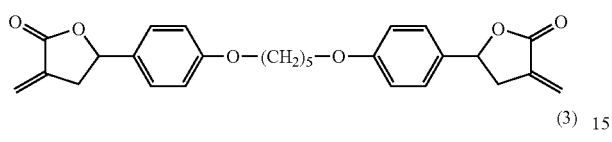 (2)
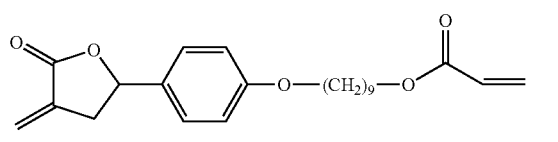 (13)
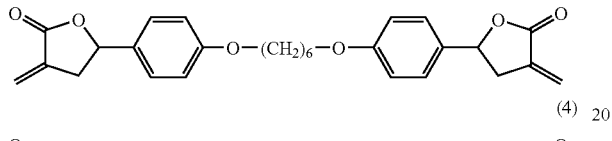 (3)
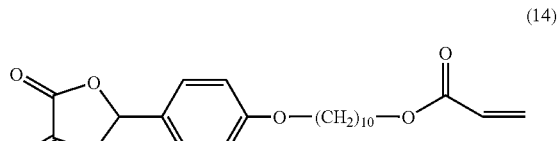 (14)
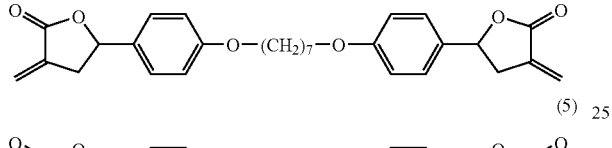 (4)
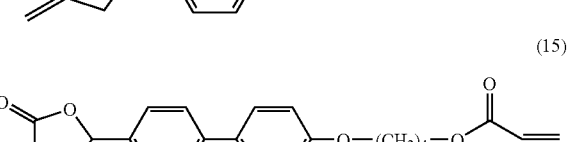 (15)
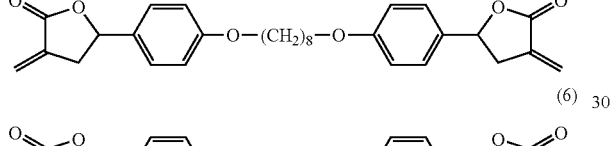 (5)
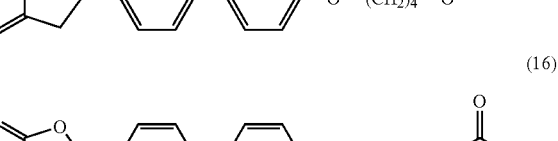 (16)
[Chemical Formula 12]
[Chemical Formula 13]
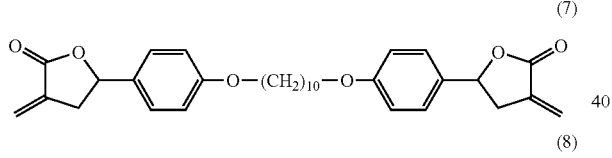 (7)
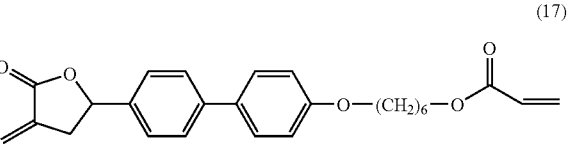 (17)
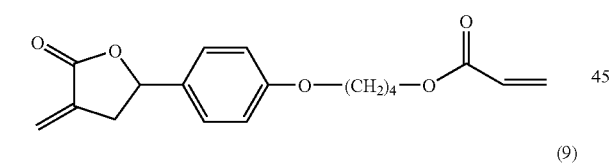 (8)
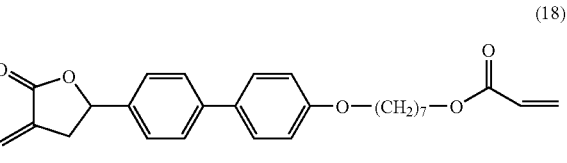 (18)
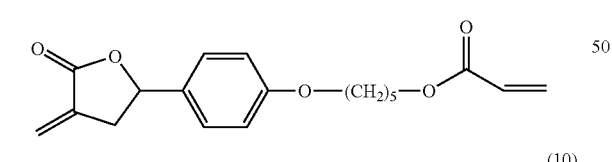 (9)
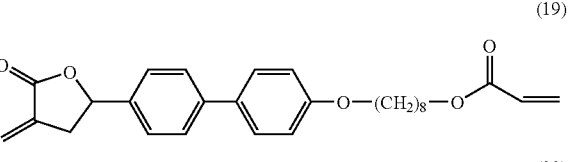 (19)
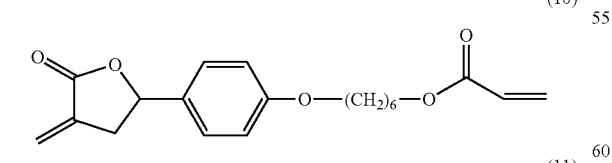 (10)
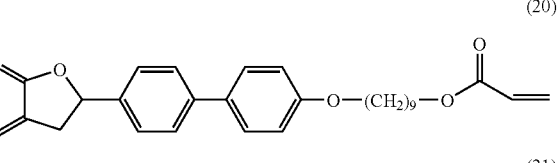 (20)
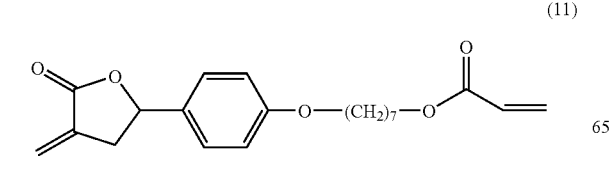 (11)
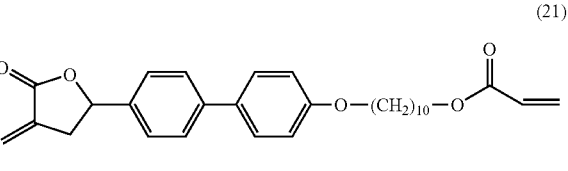 (21)

-continued

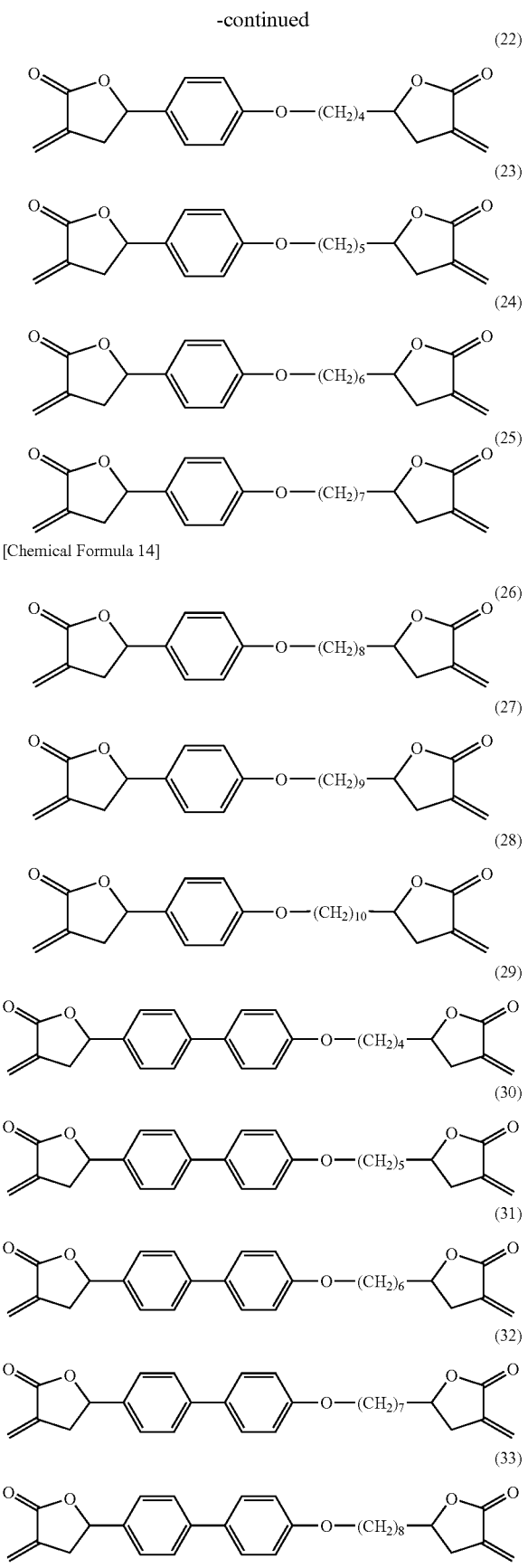

[Chemical Formula 14]

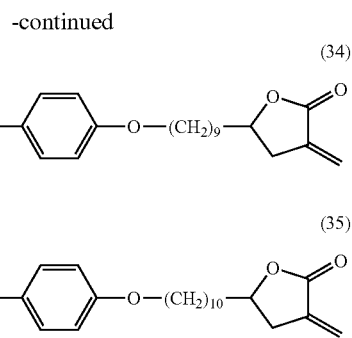

[Synthesis of Bifunctional Polymerizable Compound]

The bifunctional polymerizable compound according to the present invention can be synthesized by combining procedures in organic synthesis chemistry, and no particular limitation is imposed on its synthesis process.

For example, the α-methylene-γ-butyrolactone structure can be synthesized using the technique of Talaga et al. (P. Talaga, M. Schaeffer, C. Benezra and J. L. Stampf, Synthesis, 530 (1990)), which is represented by the below-described synthesis scheme (S1). This technique is the process that reacts 2-(bromomethyl)propenoic acid with an aldehyde or ketone by using $SnCl_2$.

It is to be noted that 2-(bromomethyl)propenoic acid can be obtained by the process proposed by K. Ramarajan et al. (K. Ramarajan, K. Kamalingam, D. J. O'Donnell and K. D. Berlin, Organic Syntheses, vol. 61, 56-59 (1983)).

[Chemical Formula 15]

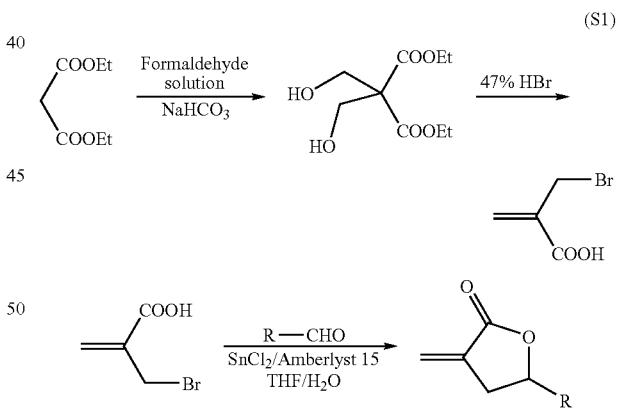

wherein R represents a monovalent organic group, and "Amberlyst 15" is a registered trademark of Rohm & Haas Company.

In this reaction, the α-methylene-γ-butyrolactone structure can also be obtained by using, instead of the aldehyde or ketone, its corresponding acetal or ketal (see a synthesis scheme (S2)).

As the acetal or ketal, a dimethylacetal group, diethylacetal group, 1,3-dioxane group, 1,3-dioxorane group or the like can be mentioned.

[Chemical Formula 16]

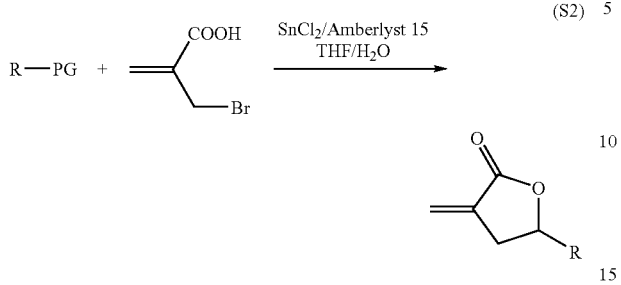

(S2)

wherein PG represents the following formulas (i) to (iv).

[Chemical Formula 17]

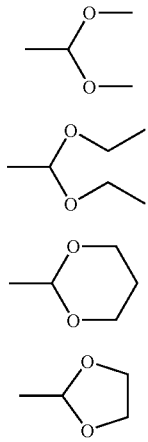

(i)

(ii)

(iii)

(iv)

As the below-described schemes (S3) to (S4), synthesis processes of polymerizable compounds represented by the formula [1b] will be shown.

The following scheme (S3) applies to the case that in the formula [1b], $X^1$ is a single bond or phenyl, and n is from 4 to 10, and M is an acrylate.

[Chemical Formula 18]

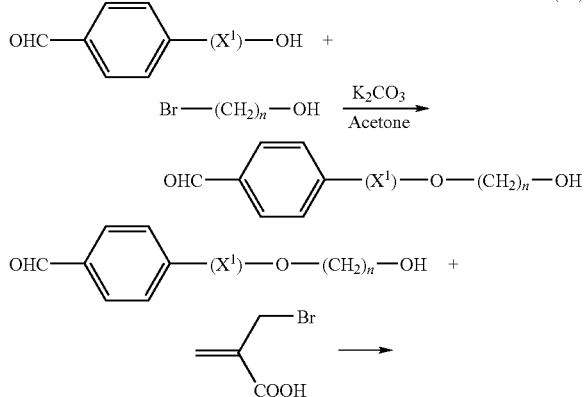

(S3)

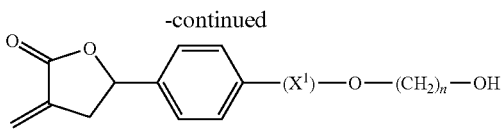

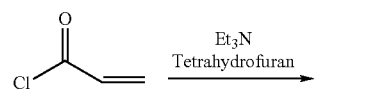

The following scheme (S4) corresponds to the case that in the formula [1b], $X^1$ is a single bond or phenyl, and n is from 4 to 10, and M is a γ-butyrolactone.

[Chemical Formula 19]

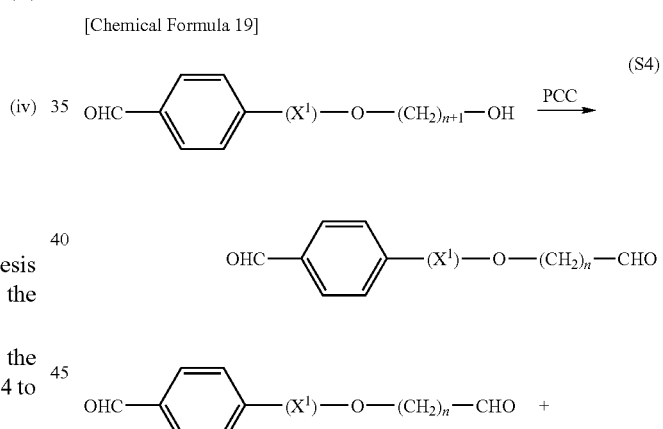

(S4)

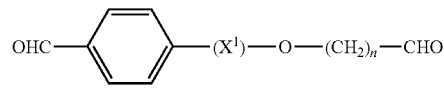

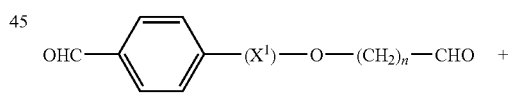

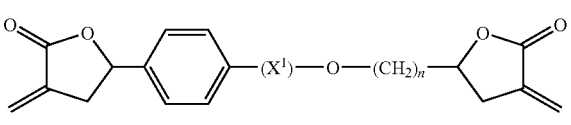

As the below-described schemes (S5) to (S6), synthesis processes of polymerizable compounds represented by the formula [1a] will be shown.

The following scheme (S5) applies to the case that in the formula [1a], $X^1$ and $X^2$ are each a single bond or phenyl, $X^3$ is phenyl, n is from 4 to 10, and M is a γ-butyrolactone.

[Chemical Formula 20]

(S5)

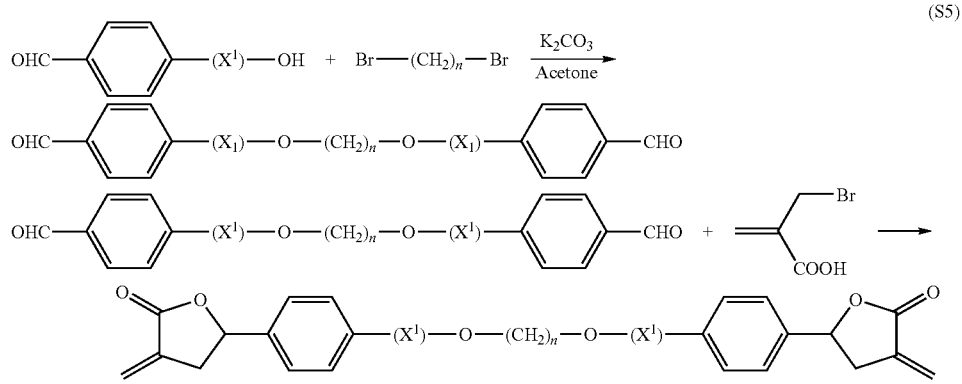

The following scheme (S6) corresponds to the case that in the formula [1a], $X^1$ and $X^2$ are each a single bond or phenyl, $X^3$ is phenyl, n is from 4 to 10, and M is an acrylate.

[Chemical Formula 21]

(S6)

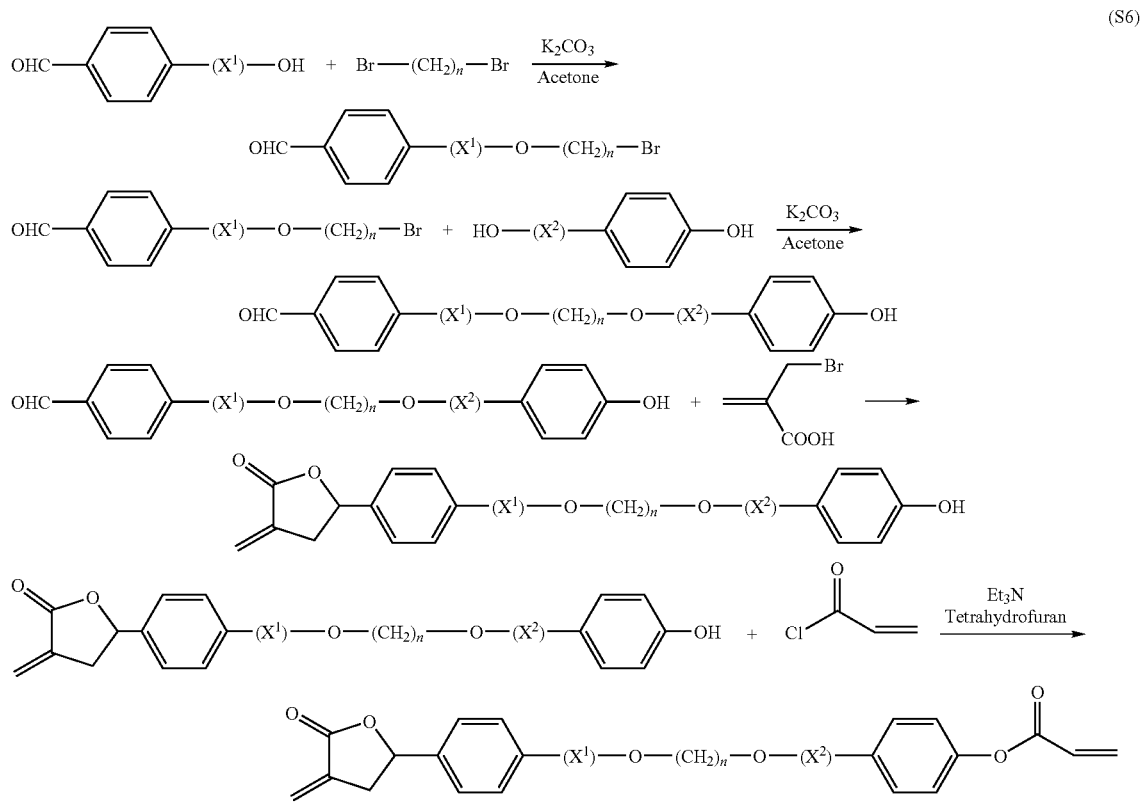

[Polymerizable Liquid Crystal Composition]

The polymerizable composition according to the present invention contains the bifunctional polymerizable compound of the formula [1] and the polymerizable liquid crystal compound.

The polymerizable liquid crystal compound can be any desired compound insofar as it has a polymerizable group, shows liquid crystallinity, and can be either monofunctional or bifunctional. As the polymerizable liquid crystal compound, a nematic liquid crystal, ferroelectric liquid crystal, commercial liquid crystal compound or the like can be mentioned. However, preferred is a polymerizable liquid crystal compound having one or two acrylate groups in its molecule or a polymerizable liquid crystal compound having a lactone ring in its molecule because a polymer (film) obtained from the corresponding polymerizable liquid crystal composition exhibits more stable anisotropy. Further, the polymerizable liquid crystal compound for use in the present invention may preferably exhibit a liquid crystal phase which is enantiotropic (stable) at room temperature.

In view of these, it is particularly preferred to use, as a polymerizable liquid crystal compound, a polymerizable liquid crystal compound represented by the formula [4], a polymerizable liquid crystal compound represented by the formula [5], or a mixture thereof.

[Chemical Formula 22]

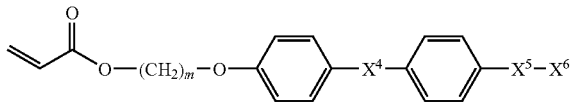

[4]

wherein $X^4$ is a single bond, —COO—, —HC=N— or —C=C—, $X^5$ is a single bond or benzene ring, $X^6$ is a hydrogen atom, cyano group, methoxy group or fluorine atom, and m stands for an integer of from 2 to 10.

[Chemical Formula 23]

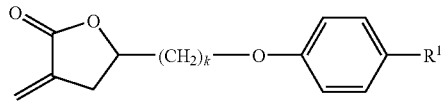

[5]

wherein $R^1$ is an organic group represented by the formula [6] or [7], and k stands for an integer of from 2 to 9.

[Chemical Formula 24]

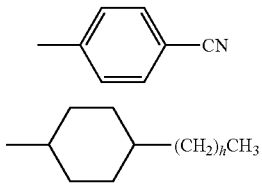

[6]

[7]

wherein h stands for an integer of from 4 to 8.

In the formulas [4] and [5], the repeating units of methylene group as represented by —$(CH_2)_m$— and —$(CH_2)_k$— are also spacer moieties, the repeat number m is an integer of from 2 to 10, preferably an integer of from 4 to 6, and the repeat number k is an integer of from 2 to 9, preferably an integer of from 4 to 6.

In the formula [4], $X^4$ is a single bond, —COO—, —HC=N— or —C=C—, with a single bond or —COO— being preferred.

$X^6$ is a hydrogen atom, cyano group, methoxy group or fluorine atom, with a hydrogen atom or cyano group being preferred.

In the formula [7], h is an integer of from 4 to 8, preferably an integer of from 6 to 8.

The above-described specific polymerizable liquid crystalline compound, which is represented by the formula [4] and has an acrylic group, can be obtained, for example, by using the process described in JP-A 62-70407.

The above-described polymerizable liquid crystal compound represented by the formula [5] can be obtained by using an aldehyde represented by the following formula [8] as the aldehyde (R—CHO) in the above-mentioned synthesis scheme (S1).

[Chemical Formula 25]

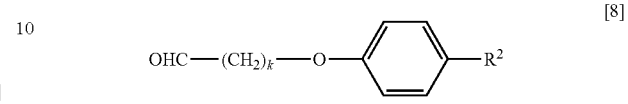

[8]

wherein k has the same meaning as defined above, and $R^2$ is a group represented by the formula [6] or [7].

[Chemical Formula 26]

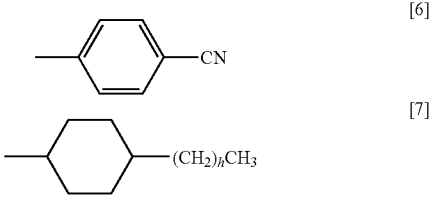

[6]

[7]

wherein h stands for an integer of from 4 to 8.

The compound represented by the formula [8] can be obtained by oxidation of a primary alcohol compound. This primary alcohol compound can in turn be obtained by reacting a bromoalcohol and a phenol compound with each other. The bromoalcohol and phenol compound to be used are commercial products, and therefore, are readily available. Details of their reaction are shown in below-described synthesis scheme (S7).

When k=3 or 4, it is preferred to conduct the protection of the hydroxyl group with tetrahydropyranyl ether or the like beforehand so that the intramolecular cyclization reaction of the bromoalcohol compound can be avoided to improve the yield.

[Chemical Formula 27]

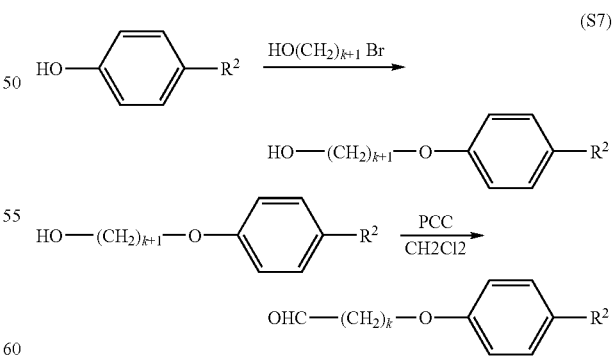

(S7)

wherein k and $R^2$ have the same meanings as defined above, and PCC represents pyridinium chlorochromate.

The mixing ratio of the bifunctional polymerizable compound represented by the formula [1] to the polymerizable liquid crystal compound represented by the formula [4] or [5]

is optional, but the bifunctional polymerizable compound represented by the formula [1] may be added in an amount of preferably from 2 to 15 parts by weight, more preferably from 5 to 10 parts by weight per 100 parts by weight of (the sum of) the polymerizable liquid crystal compound(s).

It is to be noted that in the polymerizable liquid crystal composition according to the present invention, two or more of bifunctional polymerizable compounds represented by the formula [1] and two or more of polymerizable liquid crystal compounds represented by the formula [4] and formula [5] may be used, respectively.

The polymerizable liquid crystal composition, which contains the polymerizable liquid crystal compound represented by the formula [4] and/or the formula [5] and the bifunctional polymerizable compound represented by the formula [1], often exhibits a liquid crystal phase such as a smectic phase or nematic phase, and this property is useful in application fields making use of optical anisotropy such as polarizer plates and retarder plates.

Specific examples of the polymerizable liquid crystal compound represented by the above formula [4] or [5] include, but are not limited to, the following compounds (36) to (61).

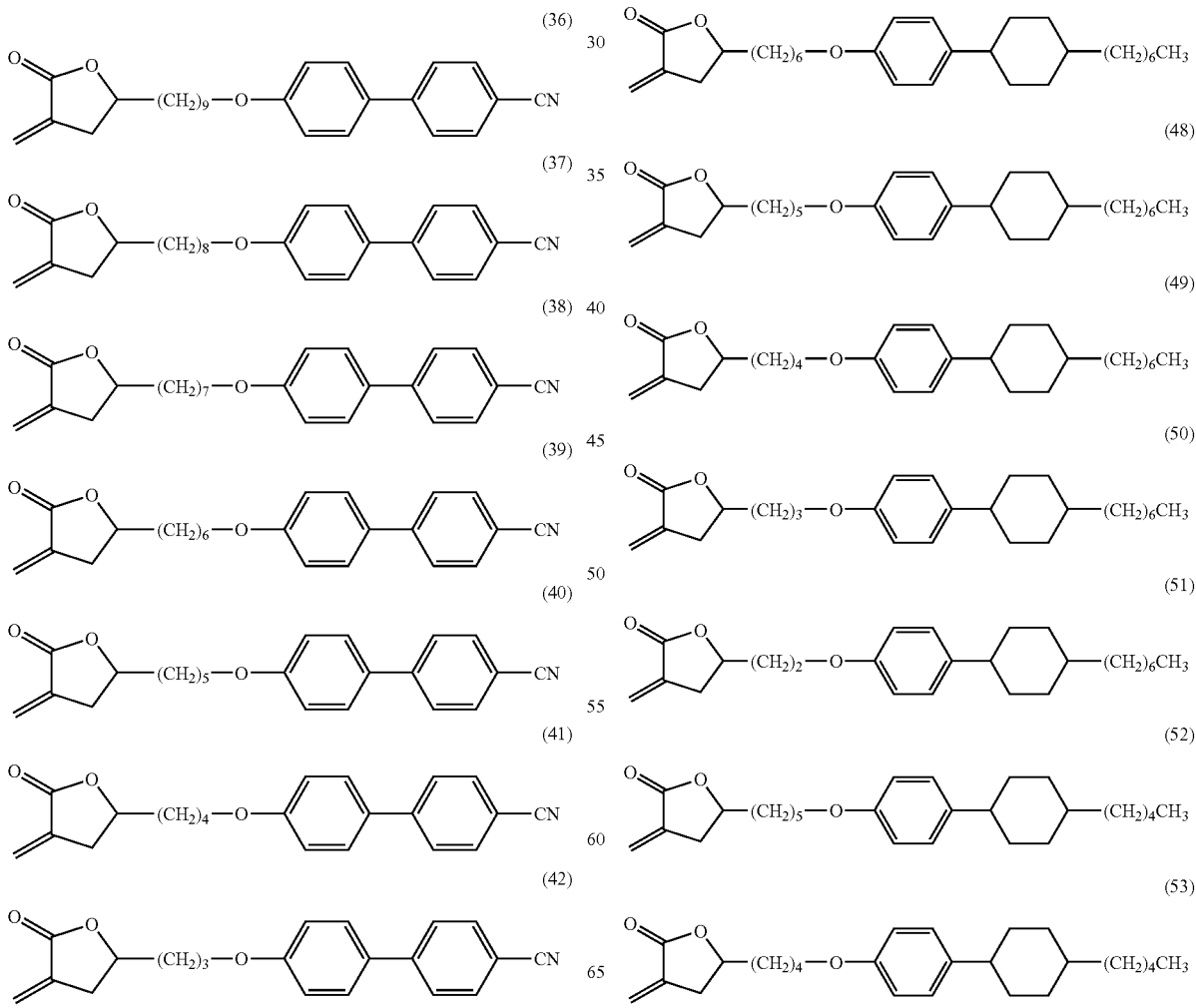

-continued

[Chemical Formula 30]

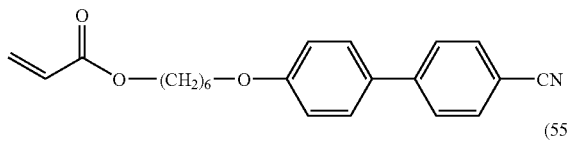
(54)

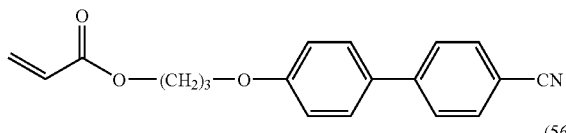
(55)

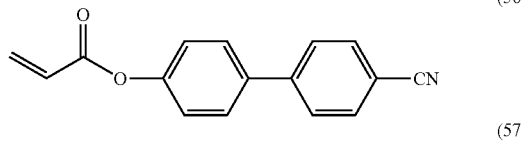
(56)

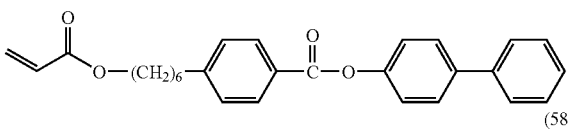
(57)

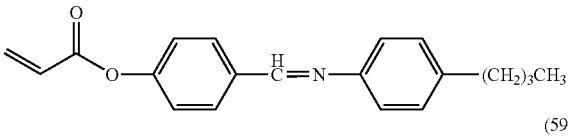
(58)

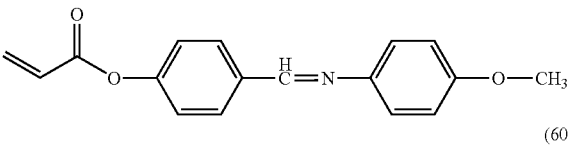
(59)

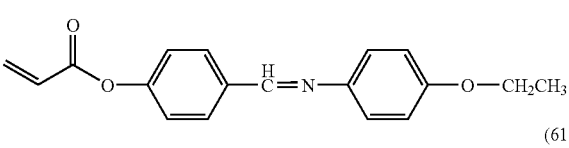
(60)

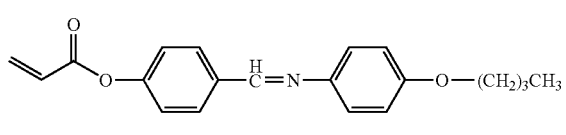
(61)

To the polymerizable liquid crystal composition according to the present invention, a photopolymerization initiator, thermal polymerization initiator or photosensitizer can be added with a view to improving its polymerization reactivity.

Examples of the photopolymerization initiator include benzoin ethers such as benzoin methyl ether, benzophenones such as benzophenone, acetophenones such as diethoxyacetophenone, and benzyl ketals such as benzyl dimethyl ketal. A plurality of such photopolymerization initiators may be used in combination. The photopolymerization initiator may be added in an amount of preferably not more than 5 parts by weight, more preferably from 0.5 to 2.0 parts by weight per 100 parts by weight of the sum of the bifunctional polymerizable compound represented by the formula [1] and the polymerizable liquid crystal compound.

Examples of the thermal polymerization initiator include 2,2'-azobisisobutyronitrile and the like. A plurality of such thermal polymerization initiators may be used in combination. The thermal polymerization initiator may be added in an amount of preferably not more than 5 parts by weight, more preferably from 0.5 to 2.0 parts by weight per 100 parts by weight of the sum of the bifunctional polymerizable compound represented by the formula [1] and the polymerizable liquid crystal compound.

Examples of the photosensitizer include anthracene photosensitizers such as anthracene. A plurality of such photosensitizers may be used in combination. The photosensitizer may be added preferably in an amount of not more than 5 parts by weight per 100 parts by weight of the sum of the bifunctional polymerizable compound represented by the formula [1] and the polymerizable liquid crystal compound.

It is to be noted that the above-described polymerization initiator may be used in combination with at least one of the thermal polymerization initiator and photosensitizer.

To the polymerizable liquid crystal composition according to the present invention, a stabilizer can also be added with a view to improving its storage stability.

Examples of the stabilizer include hydroquinone, hydroquinone monoalkyl ethers such as hydroquinone monomethyl ether, 4-t-butylcatechol, and the like. A plurality of such stabilizers may be used in combination. The stabilizer may be added preferably in an amount of not more than 0.1 parts by weight per 100 parts by weight of the sum of the bifunctional polymerizable compound represented by the formula [1] and the polymerizable liquid crystal compound.

To the polymerizable liquid crystal composition according to the present invention, an adhesion promoter can also be added with a view to improving its adhesion to a substrate.

As adhesion promoters, there can be mentioned chlorosilanes such as trimethylchlorosilane, dimethylvinylchlorosilane, methyldiphenylchlorosilane, and chloromethyldimethylchlorosilane; alkoxysilanes such as trimethylmethoxysilane, dimethyldiethoxysilane, methyldimethoxysilane, dimethylvinylethoxysilane, diphenyldimethoxysilane, and phenyltriethoxysilane; silazanes such as hexamethyldisilazane, N,N'-bis(trimethylsilyl)urea, dimethyltrimethylsilylamine, and trimethylsilylimidazole; silanes such as vinyltrichlorosilane, γ-chloropropyltrimethoxysilane, γ-aminopropyltriethoxysilane, γ-methacryloxypropyltrimethoxysilane, γ-glycidoxypropyltrimethoxysilane, and γ-(N-piperidinyl)propyltrimethoxysilane; heterocyclic compounds such as benzotriazole, benzimidazole, indazole, imidazole, 2-mercaptobenzimidazole, 2-mercaptobenzothiazole, 2-mercaptobenzooxazole, urazole, thiouracil, mercaptoimidazole, and mercaptopyrimidine; urea compounds such as 1,1-dimethylurea and 1,3-dimethylurea, and thiourea compounds.

A plurality of such adhesion promoters may be used in combination. The adhesion promoter may be added preferably in an amount of not more than 1 part by weight per 100 parts by weight of the sum of the bifunctional polymerizable compound represented by the formula [1] and the polymerizable liquid crystal compound.

Furthermore, to the polymerizable liquid crystal composition according to the present invention, an organic solvent can also be added for a viscosity adjustment or the like. In this case, no problem arises even if no liquid crystallinity is exhibited in a state that an organic solvent is contained.

Examples of the organic solvent include ethers such as tetrahydrofuran and dioxane; aromatic hydrocarbons such as benzene, toluene and xylene; polar solvents such as N,N-dimethylformamide and N-methyl-2-pyrrolidone; esters such as ethyl acetate, butyl acetate and ethyl lactate; alkoxy esters such as methyl 3-methoxypropionate, methyl 2-methoxypropionate, ethyl 3-methoxypropionate, ethyl 2-methoxypropionate, ethyl 3-ethoxypropionate and ethyl 2-ethoxypropionate; glycol dialkyl ethers such as ethylene glycol dimethyl ether and propylene glycol dimethyl ether; diglycol dialkyl ethers such as diethylene glycol dimethyl ether, diethylene glycol diethyl ether, diethylene glycol methyl ethyl ether and dipropylene glycol dimethyl ether; glycol monoalkyl ethers such as ethylene glycol monomethyl ether, ethylene glycol monoethyl ether, propylene glycol monomethyl ether and propylene glycol monoethyl ether; diglycol monoalkyl ethers such as diethylene glycol monomethyl ether, diethylene glycol monoethyl ether, dipropylene glycol monomethyl ether and dipropylene glycol monoethyl ether; glycol monoalkyl ether esters such as propylene glycol monomethyl ether acetate, carbitol acetate and ethylcellosolve acetate; and ketones such as cyclohexanone, methyl ethyl ketone, methyl isobutyl ketone and 2-heptanone.

These organic solvents can be used singly, or two or more of them can be used in combination. Among these, propylene glycol monomethyl ether, propylene glycol monomethyl ether acetate, ethyl lactate and cyclohexanone are desirable from the viewpoint of safety or the like to the global environment and working environments.

To the polymerizable liquid crystal composition according to the present invention, a surfactant can also be added with a view to improving its compatibility with a substrate. As surfactants, fluorosurfactants, silicone surfactants, nonionic surfactants and the like can be mentioned, although no particular limitation is imposed thereon. Fluorosurfactants are preferred, as they are highly effective for improving the compatibility with substrates.

Specific examples of fluorosurfactants include, but are not limited to, "EFTOP EF301, EF303, EF352" (products of Tochem Products Co., Ltd.), "MEGAFAC F171, F173, R-30" (products of Dainippon Ink and Chemicals, Incorporated), "FLUORAD FC430, FC431" (products of Sumitomo 3M Limited), and "ASAHI GUARD AG710, SURFLON S-382, SC101, SC102, SC103, SC104, SC105, SC106" (products of Asahi Glass Co., Ltd.), all of which are trade names. It is to be noted that a plurality of surfactants can be used in combination.

No particular limitation is imposed on the preparation method of the polymerizable liquid crystal composition according to the present invention, and the individual components which make up the polymerizable liquid crystal composition may be mixed together at once or may be mixed sequentially. Upon sequential mixing, the individual components may be added in any arbitrary order.

When a plurality of compounds are used as one component, a mixture obtained by combining them together in advance may be mixed with the remaining components or they may be separately mixed with the remaining components.

The polymerizable liquid crystal composition according to the present invention may preferably exhibit an enantiotropic liquid crystal phase at room temperature, so that upon production of an optical isomer, the induction of unintended thermal polymerization can be avoided during photopolymerization in a liquid crystal state and the fixing of a uniformly oriented state of molecules can be facilitated. When the polymerizable liquid crystal composition contains an organic solvent, it is preferred for the composition to exhibit an enantiotropic liquid crystal phase at room temperature upon elimination of the solvent.

[Polymer and Film]

By applying light irradiation or heating treatment to the above-described polymerizable liquid crystal composition according to the present invention, a polymer can be obtained.

Further, by applying light irradiation treatment to the polymerizable liquid crystal composition in a state that it is held between two substrates or it has been coated on a substrate by a spin coating or casting method, a film can be obtained.

In this case, glass, silica, plastic sheet(s), color filter(s), plastic film(s) of triacetylcellulose (TAC) or the like, or the like can be used as the substrate or substrates. It is to be noted that as one of the two substrates, glass, a plastic sheet, a plastic film or stainless steel with a functional thin film of ITO or the like formed thereon or a belt or drum with a metal such as chromium or aluminum plated or vapor-deposited thereon can be used.

With a view to providing the resultant film with improved orientation, it is preferred to apply alignment treatment to each substrate to be used. As a method for such alignment treatment, a method can be suitably chosen and used from known methods such as the method that coats an alignment material containing a polyimide precursor, polyimide, polyvinyl cinnamate or the like and subjects the thus-coated material to alignment treatment by rubbing or irradiation of polarized ultraviolet rays, the method that forms an obliquely-deposited film of silicon dioxide, and the method that forms a Langmuir film.

According to the method that holds the polymerizable liquid crystal composition between two substrates, a cell is prepared with a space formed between two substrates by a spacer or the like, the polymerizable liquid crystal composition is injected into the cell by a method that makes use of capillary action or by a method that depressurizes the space of the cell, and light is then irradiated to polymerize the composition.

As a simpler method, there is also a method that places the polymerizable liquid crystal composition on a substrate on which a spacer or the like is arranged, lays another substrate over the first-mentioned substrate, and then irradiates light to polymerize the composition.

In this case, the polymerizable liquid crystal composition may be used in a form that it is fluidized beforehand, or may be placed on the substrate and may then be fluidized by heating or the like. It is, however, necessary to fluidize the polymerizable liquid crystal composition before the another substrate is laid over.

In the method that coats the polymerizable liquid crystal composition, a step that heats by a hot plate or the like may be added as needed between the step that coats the polymerizable liquid crystal composition and the step that polymerizes it by light or heat. Especially when a polymerizable liquid crystal composition containing an organic solvent is used, this step is effective as a method for removing an organic solvent from the composition.

In each of the above-described methods, a film having oriented optical anisotropy can be obtained by polymerizing the polymerizable liquid crystal composition in a state that it exhibits a liquid crystal phase.

To obtain a polymer in a multi-domain state in which each domain has a different orientation from its adjacent domain, it is possible to use a method that achieves a multi-domain state in the step of polymerization or a method that conducts alignment treatment of a substrate to achieve a multi-domain state.

As a method that achieves a multi-domain state in the step of polymerization, there can be mentioned a method that exposes the polymerizable liquid crystal composition, which is in a liquid crystal state, to ultraviolet rays to form polymerized domains and polymerizes the remaining domains in an isotropic liquid crystal state, or a like method.

As a method that conducts alignment treatment of a substrate to achieve a multi-domain state, on the other hand, there can be mentioned a method that applies, via a mask, rubbing to an alignment material formed on a substrate, a method that irradiates, via a mask, ultraviolet rays to an alignment material formed on a substrate, or a like method.

By such a method, it is possible to obtain a substrate formed in a multi-domain state that the domains exposed to ultraviolet rays form portions subjected to alignment treatment and the remaining domains form untreated portions. The polymerizable liquid crystal composition formed on the substrate, which has been formed into the multi-domain state, is in a multi-domain state under the influence of the alignment material layer.

It is to be noted that a method making use of an electric field or a magnetic field may be used in place of the above-described alignment treatment method.

The use of the polymerizable liquid crystal composition according to the present invention makes it possible to obtain a film having optical anisotropy, and this film can be suitably used as a polarizer plate, a retarder plate or the like. Moreover, this film is good in transparency at elevated temperatures, and therefore, can be suitably used in electronic equipment used under a high-temperature environment, such as an in-car display device.

EXAMPLES

The present invention will hereinafter be described more specifically based on Synthesis Examples, Examples and Comparative Examples, but the present invention shall not be limited to the following Examples. It is to be noted that measurement methods and measurement conditions for respective physical properties in the Examples are as follows.

[1] NMR

A compound was dissolved in deuterated chloroform ($CDCl_3$) or deuterated dimethyl sulfoxide (DMSO-d6), and using a nuclear magnetic resonance system (manufactured by JOEL Ltd.), a $^1$H-NMR was measured at 300 MHz.

[2] Haze Value

Using a spectral haze meter ("TC-1800H") manufactured by Tokyo Denshoku Co., Ltd., the haze value of a film was measured.

[3] Retardation Value of Film

Using a retardation measurement system ("RETS-100," manufactured by Otsuka Electronics Co., Ltd.), a retardation value was measured at 590 nm wavelength.

Synthesis Example 1

Synthesis of Polymerizable Liquid Crystal Compound (E3)

In a 100-mL pear-shaped flask fitted with a condenser, 4-cyano-4'-hydroxybiphenol (5.0 g, 25.6 mmol), 6-bromo-1-hexanol (4.6 g, 25.6 mmol), potassium carbonate (7.0 g, 50 mmol) and acetone (50 mL) were placed and combined into a mixture. The mixture was subjected to a reaction at 64° C. for 24 hours under stirring. After completion of the reaction, the solvent was distilled off under reduced pressure to obtain yellow wet solid. Subsequently, the solid and water (70 mL) were mixed. Diethyl ether (50 mL) was added, followed by extraction. The extraction was conducted three times.

An organic layer was separated, to which anhydrous magnesium sulfate was added to dry the same. Subsequent to filtration, the solvent was distilled off under reduced pressure to obtain yellow solid. The solid was dissolved in ethyl acetate (3 mL), followed by purification by silica gel column chromatography (column: "Silica Gel 60," 0.063-0.200 mm, product of Merck & Co., Inc., eluent: hexane/ethyl acetate=1/1). From the thus-obtained solution, the solvent was distilled off to obtain white solid (6.9 g). The results of a measurement of the solid by NMR are shown below. From the results, the white solid was confirmed to be an intermediate compound (A1) represented by the below-described synthesis scheme (yield: 91%).

$^1$H-NMR(DMSO-d6) δ: 1.26 (m, 6H), 1.69 (m, 2H), 3.37 (t, 2H), 4.03 (t, 2H), 7.06 (d, 2H), 7.69 (d, 2H), 7.85 (m, 4H).

[Chemical Formula 31]

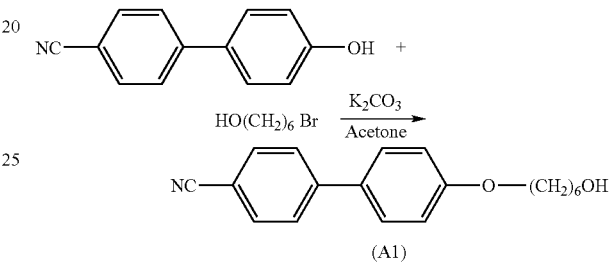

(A1)

To pyridinium chlorochromate (hereinafter called "PCC," 2.2 g, 10.0 mmol) and $CH_2Cl_2$ (30.0 mL) placed and mixed under stirring in a 200-mL three-necked flask fitted with a condenser, a solution of the above-obtained intermediate compound (A1) (2.95 g, 10.0 mmol) in $CH_2Cl_2$ (50.0 mL) was added dropwise, followed by further stirring at 40° C. for 0.5 hour. Oily matter adhered on the wall of the flask was removed. To the thus-obtained solution, diethyl ether (90 mL) was added. Subsequent to filtration under reduced pressure, the solvent was distilled off under reduced pressure to obtain dark green wet solid.

The solid was dissolved in ethyl acetate (3 mL), followed by purification by silica gel column chromatography (column: "Silica Gel 60," 0.063-0.200 mm, product of Merck & Co., Inc., eluent: hexane/ethyl acetate=1/1). From the thus-obtained solution, the solvent was distilled off to obtain colorless solid (2.8 g). The results of a measurement of the solid by NMR are shown below. From the results, the colorless solid was confirmed to be an intermediate compound (B1) represented by the below-described synthesis scheme (yield: 93%).

$^1$H-NMR($CDCl_3$) δ: 1.84 (m, 6H), 2.50 (m, 2H), 4.02 (m, 2H), 6.99 (d, 2H), 7.53 (d, 2H), 7.91 (m, 4H), 9.80 (s, 1H).

[Chemical Formula 32]

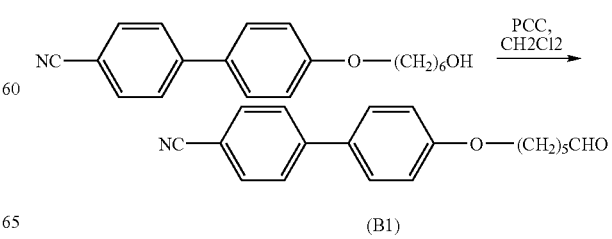

(B1)

Finally, in a 50-mL pear-shaped flask fitted with a condenser, the intermediate compound (B1) (3.0 g, 10.0 mmol) obtained as described above, 2-(bromomethyl)acrylic acid (1.65 g, 10.0 mmol), "Amberlyst (registered trademark) 15" (trade name, Rohm & Haas Company) (1.6 g), THF (16.0 mL), tin(II) chloride (1.9 g, 10.0 mmol) and purified water (4.0 mL) were placed and combined into a mixture. The mixture was subjected to a reaction at 70° C. for 7 hours under stirring. After completion of the reaction, the reaction mixture was filtered under reduced pressure, and the filtrate was mixed with purified water (30 mL). To the resulting mixture, diethyl ether (50 mL) was added, followed by extraction. The extraction was conducted three times.

To an organic layer resulted from the extraction, anhydrous magnesium sulfate was added to dry the same. Subsequent to filtration under reduced pressure, the solvent was distilled off from the resultant solution to obtain yellow solid. The solid was dissolved in ethyl acetate (2 mL), followed by purification by silica gel column chromatography (column: "Silica Gel 60," 0.063-0.200 mm, product of Merck & Co., Inc., eluent: hexane/ethyl acetate=2/1). From the thus-obtained solution, the solvent was distilled off to obtain white solid (1.5 g). As a result of a measurement of the solid by NMR, the white solid was confirmed to be the target polymerizable liquid crystal compound (E3) (yield: 41%).

$^{1}$H-NMR(CDCl$_3$) δ: 1.57 (m, 6H), 1.85 (m, 2H), 2.60 (m, 1H), 3.05 (m, 1H), 4.01 (t, 2H), 4.54 (m, 1H), 5.63 (m, 1H), 6.23 (m, 1H), 7.00 (d, 2H), 7.52 (d, 2H), 7.68 (m, 4H).

Further, as a result of an observation of liquid crystallinity in the polymerizable liquid crystal compound (E3), it transformed into an isotropic liquid state at 84° C., and upon cooling, underwent a phase transition into a liquid crystal state (nematic phase) at 61° C.

[Chemical Formula 33]

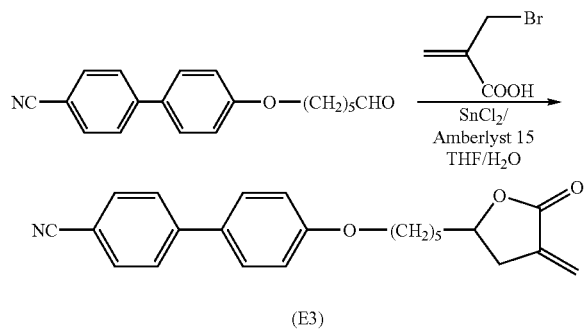

(E3)

Synthesis Example 2

Synthesis of Polymerizable Liquid Crystal Compound (E2)

[Chemical Formula 34]

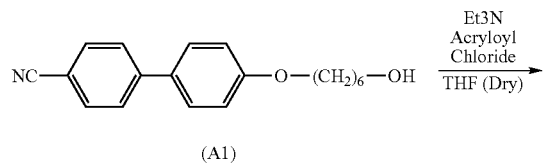

(A1)

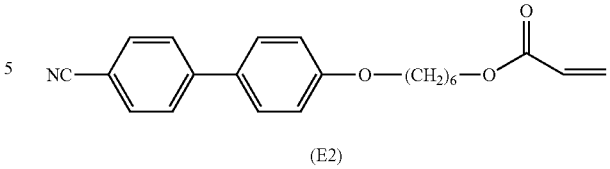

(E2)

An intermediate compound (A1) (3.0 g), which had been obtained as in Synthesis Example 1, was dissolved along with triethylamine (1.5 mL) and BHT (small amount) in THF (10 mL), followed by stirring at room temperature. Under cooling over a water bath, a solution of acryloyl chloride (0.9 mL) in THF (10 mL) was added dropwise over 15 minutes. After the dropwise addition, the reaction mixture was stirred for 30 minutes. The water bath was removed. While allowing the temperature to return to room temperature, stirring was continued overnight, and the precipitated TEA hydrochloride was filtered off. From the thus-obtained filtrate, about ¾ of THF was distilled off, followed by the addition of methylene chloride (50 mL). The organic layer was washed sequentially with a saturated aqueous solution of sodium hydrogencarbonate (50 mL), 0.5 N—HCl (50 mL) and a saturated saline solution (50 mL). Subsequent to drying over magnesium sulfate, the solvent was distilled off to obtain the product. After recrystallization from methanol, the compound (E2) (1.7 g) was obtained.

$^{1}$H-NMR(CDCl$_3$) δ: 1.50 (m, 4H), 1.73 (m, 2H), 1.85 (m, 2H), 4.05 (t, 2H), 4.20 (t, 2H), 5.82 (d, 1H), 6.15 (m, 1H), 6.41 (d, 1H), 6.99 (d, 2H), 7.55 (d, 2H), 7.66 (m, 4H).

Synthesis Example 3

Synthesis of Polymerizable Liquid Crystal Compound (E1)

[Chemical Formula 35]

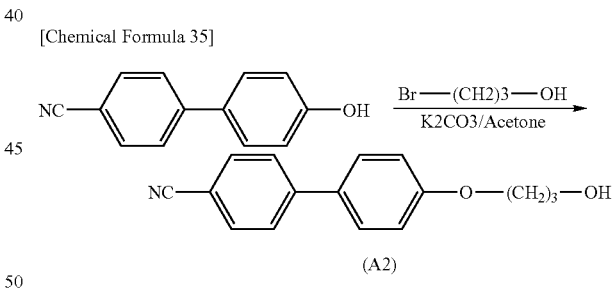

(A2)

In a 500-mL pear-shaped flask fitted with a condenser, 4-cyano-4'-hydroxybiphenol (9.8 g, 50.0 mmol), 3-bromo-1-propanol (7.0 g, 50.0 mmol), potassium carbonate (13.8 g, 100 mmol) and acetone (150 mL) were placed and combined into a mixture. The mixture was subjected to a reaction at 64° C. for 48 hours under stirring. After completion of the reaction, the solvent was distilled off under reduced pressure to obtain yellow wet solid. Subsequently, the solid and water (140 mL) were mixed. Diethyl ether (100 mL) was added, followed by extraction. The extraction was conducted three times. An organic layer was separated, to which anhydrous magnesium sulfate was added to dry the same. Subsequent to filtration, the solvent was distilled off under reduced pressure to obtain yellow solid. Using a 2/1 mixed solvent of hexane and ethyl acetate, the solid was purified by recrystallization to obtain white solid (8.7 g). The results of a measurement of the solid by NMR are shown below. From the results, the white solid was confirmed to be the intermediate compound (A2) (yield: 70%).

$^1$H-NMR(CDCl$_3$) δ: 2.09 (m, 2H), 3.90 (t, 2H), 4.20 (t, 2H), 6.99 (d, 2H), 7.52 (d, 2H), 7.66 (m, 4H).

[Chemical Formula 36]

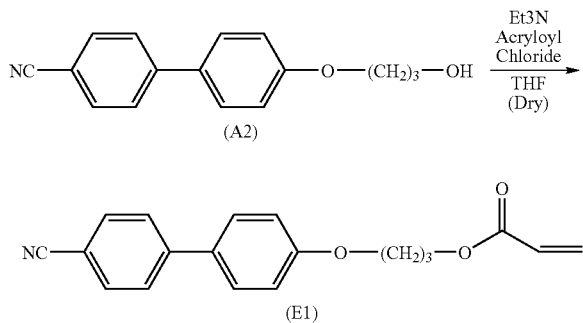

The intermediate compound (A2) (12.0 g) obtained as described above was dissolved along with triethylamine (7.7 mL) and BHT (small amount) in THF (40 mL), followed by stirring at room temperature. Under cooling over a water bath, a solution of acryloyl chloride (4.6 mL) in THF (40 mL) was added dropwise over 15 minutes. After the dropwise addition, the reaction mixture was stirred for 30 minutes. The water bath was removed. While allowing the temperature to return to room temperature, stirring was continued overnight, and the precipitated TEA hydrochloride was filtered off. From the thus-obtained filtrate, about ¾ of THF was distilled off, followed by the addition of methylene chloride (50 mL). The organic layer was washed sequentially with a saturated aqueous solution of sodium hydrogencarbonate (50 mL), 0.5 N—HCl (50 mL) and a saturated saline solution (50 mL). Subsequent to drying over magnesium sulfate, the solvent was distilled off to obtain the product. After recrystallization from ethanol, the compound (E1) (6.0 g) was obtained.

$^1$H-NMR(CDCl$_3$) δ: 2.20 (m, 2H), 4.10 (t, 2H), 4.40 (t, 2H), 5.81 (d, 1H), 6.15 (m, 1H), 6.41 (d, 1H), 6.99 (d, 2H), 7.55 (d, 2H), 7.66 (m, 4H).

[1] Bifunctional Polymerizable Compounds

Example 1

Synthesis of Compound (Z1)

(1) Synthesis of Compound (Q1)

[Chemical Formula 37]

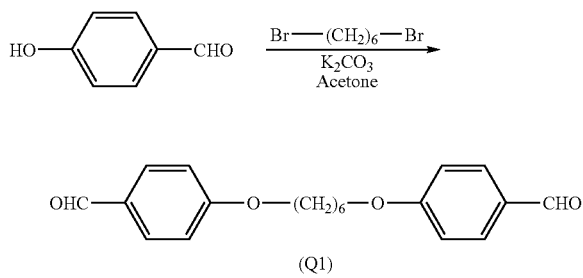

In a 500-mL pear-shaped flask fitted with a condenser, 4-hydroxybenzaldehyde (12.2 g, 100 mmol), 1,6-dibromohexane (12.2 g, 50 mmol), potassium carbonate (16.0 g, 116 mmol) and acetone (150 mL) were placed and combined into a mixture. The mixture was subjected to a reaction at 64° C. for 48 hours under stirring.

After the reaction mixture was filtered, the solvent was distilled off under reduced pressure to obtain pale-brown wet solid (15.4 g). The results of a measurement of the solid by NMR are shown below. From the results, the solid was confirmed to be the intermediate compound (Q1) shown in the above synthesis scheme (yield: 94%).

$^1$H-NMR(CDCl$_3$) δ: 1.49 (m, 4H), 1.77 (m, 4H), 4.12 (t, 4H), 7.10 (d, 2H), 7.86 (d, 2H), 9.87 (s, 2H).

(2) Synthesis of Compound (Z1)

[Chemical Formula 38]

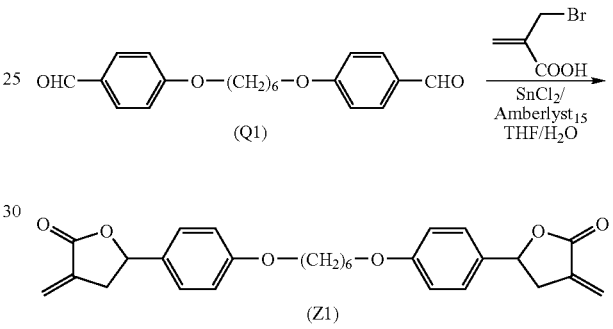

In a 100-mL pear-shaped flask fitted with a condenser, the intermediate compound (Q1) (3.3 g, 10.0 mmol) obtained as described above, 2-(bromomethyl)acrylic acid (3.3 g, 20.0 mmol), "Amberlyst (registered trademark) 15" (trade name, Rohm & Haas Company) (3.0 g), tetrahydrofuran (hereinafter called "THF," 32.0 mL), tin(II) chloride (3.8 g, 20.0 mmol) and purified water (8.0 mL) were placed and combined into a mixture. The mixture was subjected to a reaction at 70° C. for 24 hours under stirring. After completion of the reaction, the reaction mixture was filtered under reduced pressure, and the filtrate was mixed with purified water (60 mL). To the resulting mixture, diethyl ether (70 mL) was added, followed by extraction. The extraction was conducted three times. To an organic layer resulted from the extraction, anhydrous magnesium sulfate was added to dry the same. Subsequent to filtration under reduced pressure, the solvent was distilled off from the resultant solution to obtain pale brown solid.

The solid was dissolved in ethyl acetate (10 mL), followed by purification by silica gel column chromatography (column: "Silica Gel 60," 0.063-0.200 mm, product of Merck & Co., Inc., eluent: hexane/ethyl acetate=1/1) to obtain white solid (2.6 g). As a result of a measurement of the solid by NMR, the white solid was confirmed to be the target polymerizable liquid crystal compound (Z1) (yield: 55%).

$^1$H-NMR(CDCl$_3$) δ: 1.54 (m, 4H), 1.80 (m, 4H), 2.94 (m, 2H), 3.35 (m, 2H), 3.97 (t, 4H), 5.47 (m, 2H), 5.68 (m, 2H), 6.30 (m, 2H), 6.88 (d, 4H), 7.26 (d, 4H).

Example 2

Synthesis of Compound (Z2)

(1) Synthesis of Compound (P2)

[Chemical Formula 39]

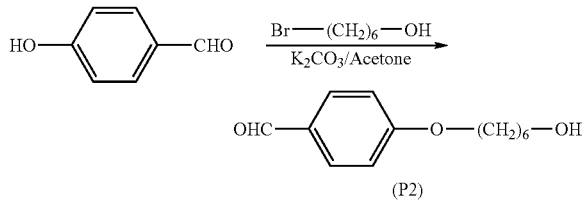

In a 100-mL pear-shaped flask fitted with a condenser, 4-hydroxybenzaldehyde (6.1 g, 50 mmol), 6-bromo-1-hexanol (9.1 g, 50 mmol), potassium carbonate (13.8 g, 100 mmol) and acetone (100 mL) were placed and combined into a mixture. The mixture was subjected to a reaction at 64° C. for 24 hours under stirring. After completion of the reaction, the solvent was distilled off under reduced pressure to obtain yellow wet solid. Subsequently, the solid and water (70 mL) were mixed. Diethyl ether (50 mL) was added, followed by extraction. The extraction was conducted three times.

An organic layer was separated, to which anhydrous magnesium sulfate was added to dry the same. Subsequent to filtration, the solvent was distilled off under reduced pressure to obtain yellow solid. The solid was dissolved in ethyl acetate (5 mL), followed by purification by silica gel column chromatography (column: "Silica Gel 60", 0.063-0.200 mm, product of Merck & Co., Inc., eluent: hexane/ethyl acetate=2/1). From the thus-obtained solution, the solvent was distilled off to obtain white solid (7.4 g). The results of a measurement of the solid by NMR are shown below. From the results, the white solid was confirmed to be the intermediate compound (P2) shown in the above-described synthesis scheme (yield: 67%).

$^1$H-NMR(DMSO-d6) δ: 1.55 (m, 4H), 1.62 (m, 2H), 1.84 (m, 2H), 3.67 (t, 2H), 4.05 (t, 2H), 7.00 (d, 2H), 7.84 (d, 2H), 9.88 (s, 1H).

(2) Synthesis of Compound (Q2)

[Chemical Formula 40]

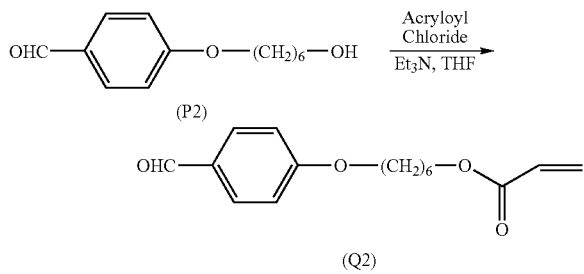

In a 50-mL three-necked flask, the compound (P2) (2.2 g) obtained as described above, triethylamine (1.7 mL), butylhydroxytoluene (hereinafter called "BHT") (0.2 mg) and THF (10 mL) were mixed into a solution. To the solution, a solution of acryloyl chloride (1.0 mL) in THF (10 mL) was added dropwise over 15 minutes under stirring. During the dropwise addition, the three-necked flask was chilled over a water bath (water temperature: 20° C.). After the dropwise addition, stirring was continued for 30 minutes in the same state. The flask was taken out of the water bath and then purged with nitrogen. Stirring was continued at room temperature for 3 hours to conduct a reaction. The reaction mixture was filtered, the filtrate was concentrated to a ¾ volume under reduced pressure, and methylene chloride (100 mL) was then added to the concentrate. The resulting solution was washed sequentially with a saturated solution of sodium hydrogencarbonate (100 mL), 0.5 N hydrochloric acid (100 mL) and a saturated saline solution (100 mL). Subsequent to drying over magnesium sulfate, the solvent was distilled off to obtain yellow solid. The solid was dissolved in ethyl acetate (3 mL), followed by purification by silica gel column chromatography (column: "Silica Gel 60", 0.063-0.200 mm, product of Merck & Co., Inc., eluent: hexane/ethyl acetate=2/1). From the thus-obtained solution, the solvent was distilled off to obtain white solid (2.0 g). The results of a measurement of the solid by NMR are shown below. From the results, the white solid was confirmed to be the intermediate compound (Q2) shown in the above-described synthesis scheme (yield: 72%).

$^1$H-NMR(CDCl$_3$) δ: 1.48 (m, 4H), 1.75 (m, 2H), 1.85 (m, 2H), 4.05 (t, 2H), 4.18 (t, 2H), 5.81 (d, 1H), 6.14 (m, 1H), 6.37 (d, 1H), 6.99 (m, 2H), 7.82 (m, 2H), 9.88 (s, 1H).

(3) Synthesis of Compound (Z2)

[Chemical Formula 41]

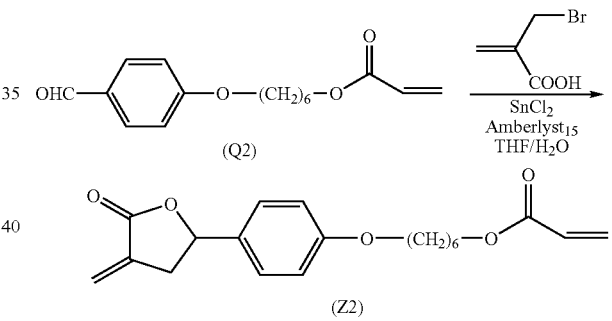

In a 50-mL pear-shaped flask fitted with a condenser, the intermediate compound (Q2) (2.0 g, 7 mmol) obtained as described above, 2-(bromomethyl)acrylic acid (1.2 g, 7.0 mmol), "Amberlyst (registered trademark) 15" (trade name, Rohm & Haas Company) (1.2 g), THF (8.0 mL), tin(II) chloride (1.4 g, 7 mmol) and purified water (2.0 mL) were placed and combined into a mixture. The mixture was subjected to a reaction at 70° C. for 24 hours under stirring. After completion of the reaction, the reaction mixture was filtered under reduced pressure, and the filtrate was mixed with purified water (60 mL). To the resulting mixture, diethyl ether (50 mL) was added, followed by extraction. The extraction was conducted three times. To an organic layer resulted from the extraction, anhydrous magnesium sulfate was added to dry the same. Subsequent to filtration under reduced pressure, the solvent was distilled off from the resultant solution to obtain pale brown solid.

The solid was dissolved in ethyl acetate (3 mL), followed by purification by silica gel column chromatography (column: "Silica Gel 60", 0.063-0.200 mm, product of Merck & Co., Inc., eluent: hexane/ethyl acetate=2/1). From the resulting solution, the solvent was distilled off to obtain white solid (1.0 g). As a result of a measurement of the solid by NMR, the white solid was confirmed to be the target polymerizable liquid crystal compound (Z2) (yield: 40%).

$^1$H-NMR(CDCl$_3$) δ: 1.48 (m, 4H), 1.75 (m, 4H), 2.94 (m, 1H), 3.39 (m, 1H), 3.95 (t, 2H), 4.17 (t, 2H), 5.45 (t, 1H), 5.68 (m, 1H), 5.83 (m, 1H), 6.13 (m, 1H), 6.30 (m, 1H), 6.40 (d, 1H), 6.88 (d, 2H), 7.26 (m, 2H).

Example 3

Synthesis of Compound (Z3)

(1) Synthesis of Compound (Q3)

[Chemical Formula 42]

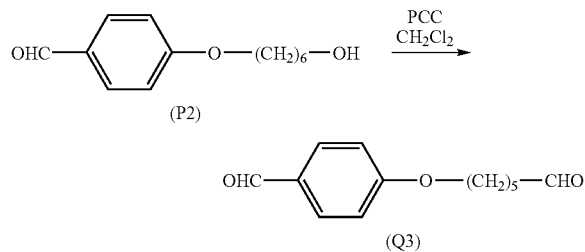

(P2)

(Q3)

To PCC (2.2 g, 10.0 mmol) and CH$_2$Cl$_2$ (25 mL) placed and mixed under stirring in a 100-mL three-necked flask fitted with a condenser, a solution of the above-obtained intermediate compound (P2) (2.2 g, 10.0 mmol) in CH$_2$Cl$_2$ (25 mL) was added dropwise, followed by further stirring at 40° C. for 0.5 hour. Oily matter adhered on the wall of the flask was removed. To the thus-obtained solution, diethyl ether (90 mL) was added. Subsequent to filtration under reduced pressure, the solvent was distilled off under reduced pressure to obtain dark-green wet solid. The solid was dissolved in ethyl acetate (3 mL), followed by purification by silica gel column chromatography (column: "Silica Gel 60", 0.063-0.200 mm, product of Merck & Co., Inc., eluent: hexane/ethyl acetate=2/1). From the thus-obtained solution, the solvent was distilled off to obtain colorless solid (1.2 g). The results of a measurement of the solid by NMR are shown below. From the results, the colorless solid was confirmed to be the intermediate compound (Q3) shown in the above-described synthesis scheme (yield: 54%).

$^1$H-NMR(CDCl$_3$) δ: 1.55 (m, 2H), 1.73 (m, 2H), 1.85 (m, 2H), 2.50 (t, 2H), 4.07 (t, 2H), 6.99 (m, 2H), 7.82 (m, 2H), 9.80 (s, 1H), 9.88 (s, 1H).

(2) Synthesis of Compound (Z3)

[Chemical Formula 43]

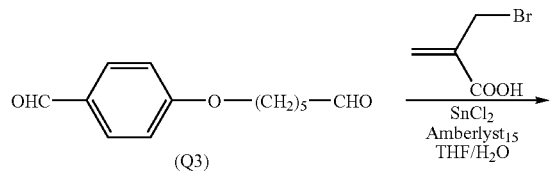

(Q3)

-continued

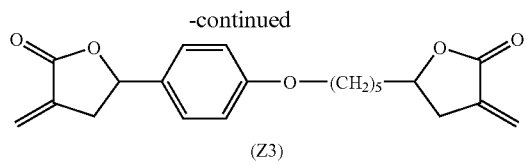

(Z3)

In a 50-mL pear-shaped flask fitted with a condenser, the intermediate compound (Q3) (1.1 g, 5 mmol) obtained as described above, 2-(bromomethyl)acrylic acid (1.7 g, 10.0 mmol), "Amberlyst (registered trademark) 15" (trade name, Rohm & Haas Company) (1.6 g), THF (16 mL), tin(II) chloride (1.9 g, 10 mmol) and purified water (4 mL) were placed and combined into a mixture. The mixture was subjected to a reaction at 70° C. for 6 hours under stirring. After completion of the reaction, the reaction mixture was filtered under reduced pressure, and the filtrate was mixed with purified water (40 mL). To the resulting mixture, diethyl ether (70 mL) was added, followed by extraction. The extraction was conducted three times. To an organic layer resulted from the extraction, anhydrous magnesium sulfate was added to dry the same. Subsequent to filtration under reduced pressure, the solvent was distilled off from the resultant solution to obtain pale brown solid. The solid was dissolved in ethyl acetate (10 mL), followed by purification by silica gel column chromatography (column: "Silica Gel 60", 0.063-0.200 mm, product of Merck & Co., Inc., eluent: hexane/ethyl acetate=2/1). From the resulting solution, the solvent was distilled off to obtain white solid (0.3 g). As a result of a measurement of the solid by NMR, the white solid was confirmed to be the target polymerizable liquid crystal compound (Z3) (yield: 14%).

$^1$H-NMR(CDCl$_3$) δ: 1.51 (m, 4H), 1.78 (m, 4H), 2.60 (m, 1H), 2.94 (m, 1H), 3.05 (m, 1H), 3.34 (m, 1H), 3.96 (t, 2H), 4.55 (m, 1H), 5.44 (m, 1H), 5.62 (m, 1H), 5.69 (m, 1H), 6.24 (m, 1H), 6.30 (m, 1H), 6.89 (d, 2H), 7.24 (m, 2H).

Example 4

Synthesis of Compound (Z4)

(1) Synthesis of Compound (P4)

[Chemical Formula 44]

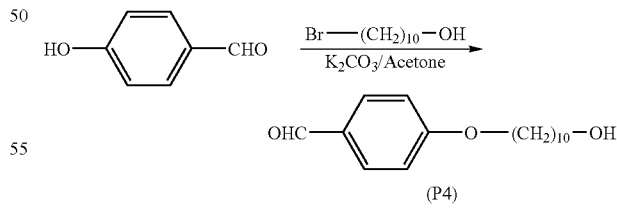

(P4)

In a 100-mL pear-shaped flask fitted with a condenser, 4-hydroxybenzaldehyde (4.6 g, 38 mmol), 10-bromo-1-decanol (9.0 g, 38 mmol), potassium carbonate (10.5 g, 76 mmol) and acetone (100 mL) were placed and combined into a mixture. The mixture was subjected to a reaction at 64° C. for 24 hours under stirring. After completion of the reaction, the solvent was distilled off under reduced pressure to obtain yellow wet solid.

The solid was dissolved in ethyl acetate (6 mL), followed by purification by silica gel column chromatography (column: "Silica Gel 60", 0.063-0.200 mm, product of Merck & Co., Inc., eluent: hexane/ethyl acetate=2/1). From the thus-obtained solution, the solvent was distilled off to obtain white solid (9.3 g). The results of a measurement of the solid by NMR are shown below. From the results, the white solid was confirmed to be the intermediate compound (P4) shown in the above-described synthesis scheme (yield: 88%).

$^1$H-NMR(CDCl$_3$) δ: 1.40 (m, 12H), 1.58 (m, 2H), 1.80 (m, 2H), 3.67 (t, 2H), 4.05 (t, 2H), 4.20 (t, 2H), 7.00 (d, 2H), 7.84 (d, 2H), 9.88 (s, 1H).

(2) Synthesis of Compound (Q4)

[Chemical Formula 45]

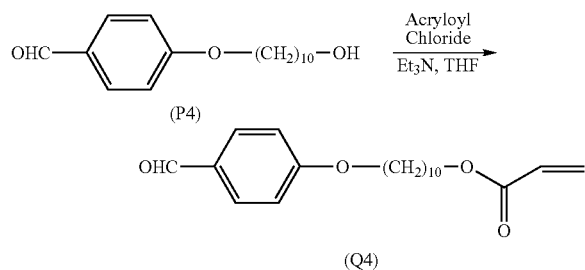

In a 200-mL three-necked flask, the compound (P4) (9.3 g) obtained as described above, triethylamine (5.8 mL), BHT (0.2 mg) and THF (50 mL) were mixed into a solution. To the solution, a solution of acryloyl chloride (3.5 mL) in THF (30 mL) was added dropwise over 15 minutes under stirring. During the dropwise addition, the three-necked flask was chilled over a water bath (water temperature: 20° C.). After the dropwise addition, stirring was continued for 30 minutes in the same state. The flask was taken out of the water bath and then purged with nitrogen. Stirring was continued at room temperature for 6 hours to conduct a reaction. The reaction mixture was filtered, the filtrate was concentrated to a ¾ volume under reduced pressure, and methylene chloride (100 mL) was then added to the concentrate. The resulting solution was washed sequentially with a saturated solution of sodium hydrogencarbonate (100 mL), 0.5 N hydrochloric acid (100 mL) and a saturated saline solution (100 mL). Subsequent to drying over magnesium sulfate, the solvent was distilled off to obtain yellow solid.

The solid was dissolved in ethyl acetate (6 mL), followed by purification by silica gel column chromatography (column: "Silica Gel 60", 0.063-0.200 mm, product of Merck & Co., Inc., eluent: hexane/ethyl acetate=2/1). From the thus-obtained solution, the solvent was distilled off to obtain yellow solid (7.5 g). The results of a measurement of the solid by NMR are shown below. From the results, the yellow solid was confirmed to be the intermediate compound (Q4) shown in the above-described synthesis scheme (yield: 68%).

$^1$H-NMR(CDCl$_3$) δ: 1.40 (m, 12H), 1.71 (m, 2H), 1.80 (m, 2H), 4.05 (t, 2H), 4.18 (t, 2H), 5.80 (d, 1H), 6.14 (m, 1H), 6.40 (d, 1H), 6.99 (m, 2H), 7.84 (m, 2H), 9.88 (s, 1H).

(3) Synthesis of Compound (Z4)

[Chemical Formula 46]

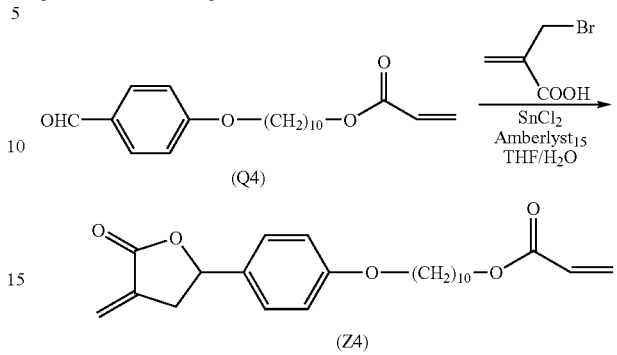

Finally, in a 50-mL pear-shaped flask fitted with a condenser, the intermediate compound (Q4) (3.3 g, 10.0 mmol) obtained as described above, 2-(bromomethyl)acrylic acid (1.65 g, 10.0 mmol), "Amberlyst (registered trademark) 15" (trade name, Rohm & Haas Company) (1.5 g), THF (15.0 mL), tin(II) chloride (1.9 g, 10.0 mmol) and purified water (3.0 mL) were placed and combined into a mixture. The mixture was subjected to a reaction at 70° C. for 24 hours under stirring. After completion of the reaction, the reaction mixture was filtered under reduced pressure, and the filtrate was mixed with purified water (100 mL). To the resulting mixture, diethyl ether (50 mL) was added, followed by extraction. The extraction was conducted three times. To an organic layer resulted from the extraction, anhydrous magnesium sulfate was added to dry the same. Subsequent to filtration under reduced pressure, the solvent was distilled off from the resultant solution to obtain pale brown solid.

The solid was dissolved in ethyl acetate (3 mL), followed by purification by silica gel column chromatography (column: "Silica Gel 60", 0.063-0.200 mm, product of Merck & Co., Inc., eluent: hexane/ethyl acetate=2/1). From the thus-obtained solution, the solvent was distilled off to obtain white solid (1.4 g). As a result of a measurement of the solid by NMR, the white solid was confirmed to be the target polymerizable liquid crystal compound (Z4) shown in the above-described synthesis scheme (yield: 35%).

$^1$H-NMR(CDCl$_3$) δ: 1.30 (m, 12H), 1.65 (m, 2H), 1.78 (m, 2H), 2.94 (m, 1H), 3.39 (m, 1H), 3.95 (t, 2H), 4.15 (t, 2H), 5.45 (t, 1H), 5.68 (m, 1H), 5.83 (m, 1H), 6.11 (m, 1H), 6.30 (m, 1H), 6.40 (d, 1H), 6.88 (d, 2H), 7.26 (m, 2H).

Example 5

Synthesis of Compound (Z5)

(1) Synthesis of Compound (P5)

[Chemical Formula 47]

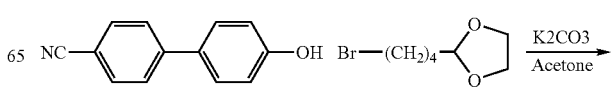

-continued

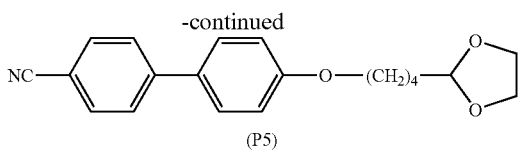
(P5)

In a 100-mL pear-shaped flask fitted with a condenser, 4-cyano-4'-hydroxybiphenol (4.7 g, 24 mmol), 2-(4-bromobutyl)-1,3-dioxolane (5.0 g, 24 mmol), potassium carbonate (6.6 g, 48 mmol) and acetone (100 mL) were placed and combined into a mixture. The mixture was subjected to a reaction at 64° C. for 24 hours under stirring. After completion of the reaction, the solvent was distilled off under reduced pressure to obtain yellow wet solid. The solid was dissolved in ethyl acetate (6 mL), followed by purification by silica gel column chromatography (column: "Silica Gel 60", 0.063-0.200 mm, product of Merck & Co., Inc., eluent: hexane/ethyl acetate=2/1). From the thus-obtained solution, the solvent was distilled off to obtain white solid (7.5 g). The results of a measurement of the solid by NMR are shown below. From the results, the white solid was confirmed to be the intermediate compound (P5) shown in the above-described synthesis scheme (yield: 97%).

$^1$H-NMR(CDCl$_3$) δ: 1.63 (m, 2H), 1.73 (m, 2H), 1.87 (m, 2H), 3.86 (t, 2H), 3.99 (m, 4H), 4.91 (t, 1H), 7.00 (d, 2H), 7.51 (d, 2H), 7.68 (m, 4H).

(2) Synthesis of Compound (Q5)

[Chemical Formula 48]

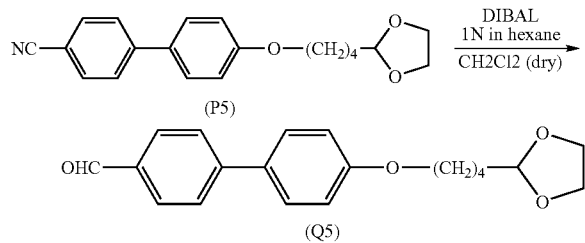

In a 50-mL three-necked flask fitted with a condenser, the intermediate compound (P5) (1.5 g, 4.6 mmol) obtained as described above and dichloromethane (10 mL) were mixed into a solution under a nitrogen atmosphere. To the solution, DIBAL (1 N, hexane solution) (7.0 mL) was added dropwise at room temperature over 15 minutes under stirring. After the dropwise addition, stirring was performed at room temperature for 6 hours to conduct a reaction. Subsequently, methanol (4.0 mL), methanol/water (1/1, 6.0 mL) and a 10% aqueous solution of hydrochloric acid (20 mL) were added dropwise little by little under stirring to quench the reaction. Diethyl ether (50 mL) was then added, followed by extraction. The extraction was conducted three times.

An organic layer was separated, to which anhydrous magnesium sulfate was added to dry the same. Subsequent to filtration, the solvent was distilled off under reduced pressure to obtain yellow solid (1.3 g). The results of a measurement of the solid by NMR are shown below. From the results, the yellow solid was confirmed to be the intermediate compound (Q5) shown in the above-described synthesis scheme (yield: 87%).

$^1$H-NMR(CDCl$_3$) δ: 1.60 (m, 2H), 1.75 (m, 2H), 1.82 (m, 2H), 3.85 (t, 2H), 4.05 (m, 4H), 4.90 (t, 1H), 7.00 (d, 2H), 7.60 (d, 2H), 7.70 (d, 2H), 7.95 (d, 2H), 10.05 (s, 1H).

(3) Synthesis of Compound (Z5)

[Chemical Formula 49]

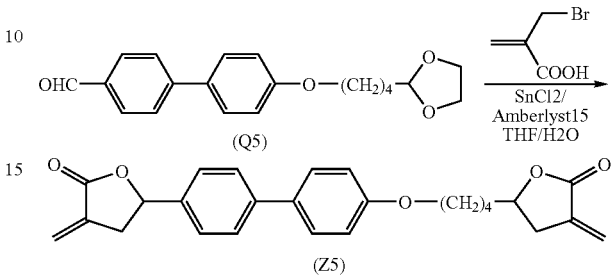

Finally, in a 30-mL pear-shaped flask fitted with a condenser, the intermediate compound (Q5) (0.7 g, 2.0 mmol) obtained as described above, 2-(bromomethyl)acrylic acid (0.7 g, 4.0 mmol), "Amberlyst (registered trademark) 15" (trade name, Rohm & Haas Company) (0.5 g), THF (5.0 mL), tin(II) chloride (0.8 g, 4.0 mmol) and purified water (1.0 mL) were placed and combined into a mixture. The mixture was subjected to a reaction at 70° C. for 6 hours under stirring. After completion of the reaction, the reaction mixture was filtered under reduced pressure, and the filtrate was mixed with purified water (60 mL). To the resulting mixture, dichloromethane (50 mL) was added, followed by extraction. The extraction was conducted three times. To an organic layer resulted from the extraction, anhydrous magnesium sulfate was added to dry the same. Subsequent to filtration under reduced pressure, the solvent was distilled off from the resultant solution to obtain pale brown solid.

The solid was recrystallized from a 2/1 mixed solvent of hexane and ethyl acetate to obtain white solid (0.4 g). As a result of a measurement of the solid by NMR, the white solid was confirmed to be the target polymerizable liquid crystal compound (Z5) shown in the above-described synthesis scheme (yield: 45%).

$^1$H-NMR(DMSO-d6) δ: 1.5 (m, 2H), 1.65 (m, 2H), 1.73 (m, 2H), 2.59 (m, 1H), 2.90 (m, 1H), 3.05 (m, 1H), 3.45 (m, 1H), 4.01 (t, 2H), 4.49 (m, 1H), 5.70 (m, 1H), 5.75 (m, 1H), 5.83 (m, 1H), 6.05 (m, 1H), 6.15 (m, 1H), 7.01 (d, 2H), 7.40 (m, 2H), 7.55 (m, 2H), 7.70 (m, 2H).

[2] Polymerizable Liquid Crystal Compositions and their Polymerization Products (Films)

The compounds used in the subsequent Examples and Comparative Examples are as follows:

[Chemical Formula 50]

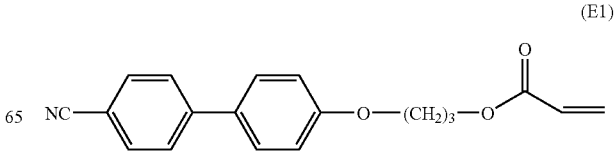
(E1)

-continued

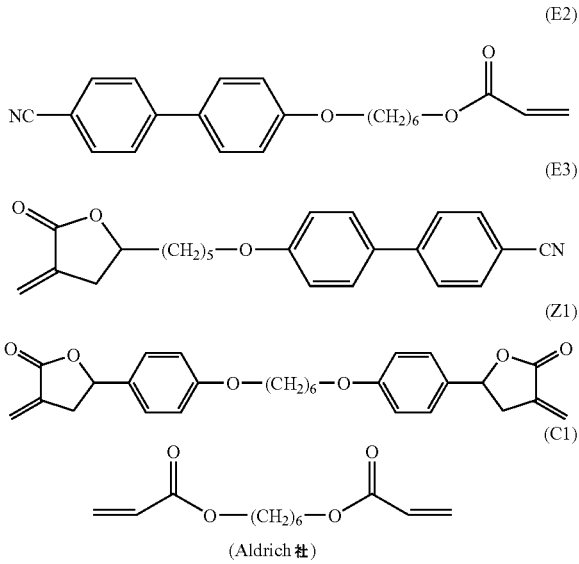

(Aldrich社)

Example 6

Polymerizable Liquid Crystal Composition and its Polymerization Product (Film)

The polymerizable liquid crystal compound (E1) (80 mg), the polymerizable liquid crystal compound (E2) (20 mg), the bifunctional polymerizable compound (Z1) obtained in Example 1 (3.0 mg), "IRGACURE 369" (trade name, photopolymerization initiator, product of Ciba-Geigy Corp.) (1.0 mg), and "FC4430" (surfactant, product of Suimitomo 3M Limited) (0.5 mg) were dissolved in cyclohexanone (0.4 g) to prepare a polymerizable liquid crystal composition.

The polymerizable liquid crystal composition was coated by spin coating (1,000 rpm, 20 seconds) on a surface of a liquid crystal alignment film applied on the substrate. After the composition was prebaked for 60 seconds on a hot plate of 80° C. temperature, it was allowed to cool down to room temperature. At that time, the polymerizable composition on the substrate was in a liquid crystal state. The substrate with the liquid crystal alignment film applied thereon, which was employed in this Example, had been obtained by applying a liquid crystal aligning agent ("SE-1410", product of Nissan Chemical Industries, Ltd.) onto an ITO surface of an ITO applied glass substrate by spin coating, baking the liquid crystal aligning agent at 230° C. temperature to form a thin film of 100 nm, and then applying rubbing processing to the thin film.

Using a high-pressure mercury vapor lamp, light of 4,000 mJ/cm$^2$ intensity was irradiated onto the coating film formed on the substrate with the liquid crystal alignment film applied thereon in a nitrogen atmosphere to polymerize the polymerizable liquid crystal composition. The thus-obtained film was 0.8 μm in thickness. By an observation of the film under a polarizing microscope, the film was confirmed to be in horizontal orientation on the substrate surface. Its retardation value was 139 nm, and its haze value was 0.2.

When the film was heated for 1 hour on a hot plate of 180° C. temperature, the retardation value was 126 nm and the haze value was 0.3. When the film was heated for 1 hour on a hot plate of 200° C. temperature, on the other hand, the retardation value was 116 nm and the haze value was 0.1.

Example 7

Polymerizable Liquid Crystal Composition and its Polymerization Product (Film)

The polymerizable liquid crystal compound (E1) (50 mg), the polymerizable liquid crystal compound (E3) (50 mg), the bifunctional polymerizable compound (Z1) obtained in Example 1 (4.0 mg), "IRGACURE 369" (trade name, photopolymerization initiator, product of Ciba-Geigy Ltd.) (1.0 mg), and "FC4430" (surfactant, product of Suimitomo 3M Limited) (0.5 mg) were dissolved in cyclohexanone (0.4 g) to prepare a polymerizable liquid crystal composition.

Using the polymerizable liquid crystal composition, a film was obtained as in Example 6. The thus-obtained film was 0.8 μm in thickness. By an observation of the film under a polarizing microscope, the film was confirmed to be in horizontal orientation on a substrate surface. Its retardation value was 129 nm, and its haze value was 0.1.

When the film was heated for 1 hour on a hot plate of 180° C. temperature, the retardation value was 122 nm and the haze value was 0.1. When the film was heated for 1 hour on a hot plate of 200° C. temperatures, on the other hand, the retardation value was 112 nm and the haze value was 0.1.

Comparative Example 1

Polymerizable Liquid Crystal Composition and its Polymerization Product (Film)

The polymerizable liquid crystal compound (E1) (80 mg), the polymerizable liquid crystal compound (E2) (20 mg), "IRGACURE 369" (trade name, photopolymerization initiator, product of Ciba-Geigy Ltd.) (1.0 mg), and "FC4430" (surfactant, product of Suimitomo 3M Limited) (0.5 mg) were dissolved in cyclohexanone (0.4 g) to obtain a polymerizable liquid crystal composition.

Using the polymerizable liquid crystal composition, a film was obtained as in Example 6. The thus-obtained film was 0.8 μm in thickness. By an observation of the film under a polarizing microscope, the film was confirmed to be in horizontal orientation on a substrate surface. Its retardation value was 127 nm, and its haze value was 0.1.

When the film was heated for 1 hour on a hot plate of 180° C. temperature, the retardation value was 42 nm and the haze value was 14.9.

Comparative Example 2

Polymerizable Liquid Crystal Composition and its Polymerization Product (Film)

The polymerizable liquid crystal compound (E1) (80 mg), the polymerizable liquid crystal compound (E2) (20 mg), a polymerizable compound (C1) which did not exhibit liquid crystallinity (3.0 mg), "IRGACURE 369" (trade name, photopolymerization initiator, product of Ciba-Geigy Ltd.) (1.0 mg), and "FC4430" (surfactant, product of Suimitomo 3M Limited) (0.5 mg) were dissolved in cyclohexanone (0.4 g) to obtain a polymerizable liquid crystal composition.

Using the polymerizable liquid crystal composition, a film was obtained as in Example 6. The thus-obtained film was 0.8 μm in thickness. By an observation of the film under a polarizing microscope, the film was confirmed to be in horizontal orientation on a substrate surface. Its retardation value was 132 nm, and its haze value was 0.1.

When the film was heated for 1 hour on a hot plate of 180° C. temperature, the retardation value was 81 nm and the haze value was 0.1. When the film was heated for 1 hour on a hot plate of 200° C. temperature, on the other hand, the retardation value was 81 nm and the haze value was 0.1.

Comparative Example 3

Polymerizable Liquid Crystal Composition and its Polymerization Product (Film)

The polymerizable liquid crystal compound (E1) (50 mg), the polymerizable liquid crystal compound (E3) (50 mg), the polymerizable compound (C1) which did not exhibit liquid crystallinity (4.0 mg), "IRGACURE 369" (trade name, photopolymerization initiator, product of Ciba-Geigy Ltd.) (1.0 mg), and "FC4430" (surfactant, product of Suimitomo 3M Limited) (0.5 mg) were dissolved in cyclohexanone (0.4 g) to obtain a polymerizable liquid crystal composition.

Using the polymerizable liquid crystal composition, a film was obtained as in Example 6. The thus-obtained film was 0.8 μm in thickness. By an observation of the film under a polarizing microscope, the film was confirmed to be in horizontal orientation on a substrate surface. Its retardation value was 137 nm, and its haze value was 0.1.

When the film was heated for 1 hour on a hot plate of 180° C. temperature, the retardation value was 109 nm and the haze value was 0.1. When the film was heated for 1 hour on a hot plate of 200° C. temperature, on the other hand, the retardation value was 90 nm and the haze value was 0.1.

The data of Examples 6 to 7 and Comparative Examples 1 to 3 are summarized in Table 1.

TABLE 1

| | Retardation value (haze value) | | |
|---|---|---|---|
| | Without baking | 180° C/1 hr | 200° C/1 hr |
| Example 6 | 139(0.2) 100% | 126(0.3) 91% | 116(0.1) 83% |
| Example 7 | 129(0.1) 100% | 122(0.1) 95% | 112(0.1) 87% |
| Comparative Example 1 | 127(0.1) 100% | 42(14.9) 33% | — |
| Comparative Example 2 | 132(0.1) 100% | 81(0.1) 61% | 81(0.1) 61% |
| Comparative Example 3 | 137(0.1) 100% | 109(0.1) 80% | 90(0.1) 66% |

As is shown in Table 1, it is appreciated that the films obtained from the polymerizable liquid crystal compositions—which contained the compound (Z1), a bifunctional polymerizable compound according to the present invention—substantially remained in their oriented state even after the baking processing at 180° C./1 hr and 200° C./1 hr, respectively, and their transparency was stable.

The invention claimed is:

1. A bifunctional polymerizable compound characterized by being represented by the following formula [1]:

[Chemical Formula 1]

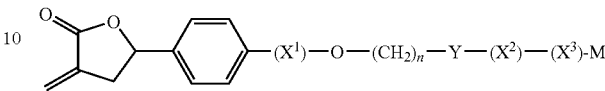

[1]

wherein $X^1$, $X^2$ and $X^3$ are each independently a single bond or a benzene ring, Y is —O— or a single bond, M is a lactone ring or an acrylate group, and n stands for an integer of from 4 to 10.

2. The bifunctional polymerizable compound according to claim 1, which is represented by the following formula [1a] or formula [1b]:

[Chemical Formula 2]

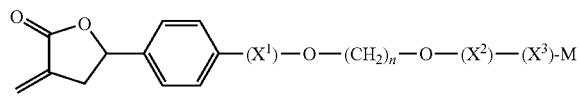

[1a]

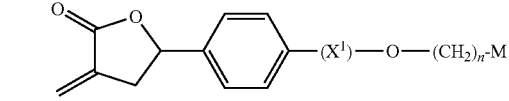

[1b]

wherein $X^1$, $X^2$, $X^3$, M and n have the same meanings as defined above.

3. The bifunctional polymerizable compound according to claim 1 or 2, wherein M is an organic group represented by the following formula [2] or [3]:

[Chemical Formula 3]

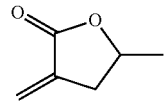

[2]

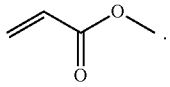

[3]

4. An additive for a polymerizable composition, comprising a bifunctional polymerizable compound as defined in claim 1.

5. A polymerizable composition comprising a bifunctional polymerizable compound as defined in claim 1.

6. A polymerizable liquid crystal composition comprising a bifunctional polymerizable compound as defined in claim 1 and a polymerizable liquid crystal compound.

7. The polymerizable liquid crystal composition according to claim 6, wherein the polymerizable liquid crystal compound has one or two acrylate groups or one lactone ring in a molecule thereof.

8. The polymerizable liquid crystal composition according to claim 6 or 7, wherein the polymerizable liquid crystal compound is a liquid crystal compound represented by the formula [4]:

[Chemical Formula 4]

[4]

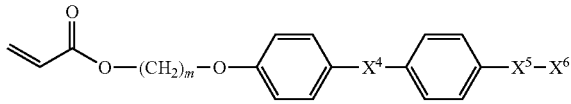

wherein $X^4$ is a single bond, —COO—, —HC=N— or —C≡C—, $X^5$ is a single bond or a benzene ring, $X^6$ is a hydrogen atom, cyano group, methoxy group or fluorine atom, and m stands for an integer of from 2 to 10.

9. The polymerizable liquid crystal composition according to claim 6 or 7, wherein the polymerizable liquid crystal compound is a liquid crystal compound represented by the formula [5]:

[Chemical Formula 5]

[5]

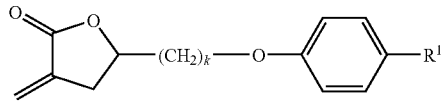

wherein $R^1$ is an organic group represented by the formula [6] or [7], and k stands for an integer of from 2 to 9,

[Chemical Formula 6]

[6]

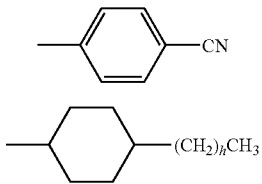

[7]

wherein h stands for an integer of from 4 to 8.

10. The polymerizable liquid crystal composition according to claim 8, further comprising a liquid crystal compound represented by the following formula [5]:

[Chemical Formula 7]

[5]

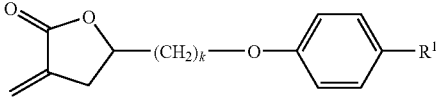

wherein $R^1$ is an organic group represented by the formula [6] or [7], and k stands for an integer of from 2 to 9,

[Chemical Formula 8]

[6]

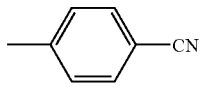

[7]

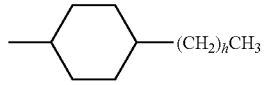

wherein h stands for an integer of from 4 to 8.

11. A polymer obtainable by polymerizing a polymerizable liquid crystal composition comprising a bifunctional polymerizable compound and a polymerizable liquid crystal compound,
wherein the bifunctional polymerizable compound is represented by the following formula [1]:

[Chemical Formula 1]

[1]

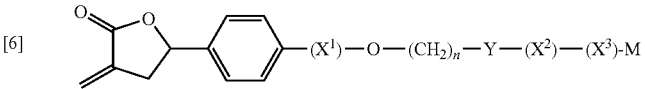

wherein $X^1$, $X^2$ and $X^3$ are each independently a single bond or a benzene ring, Y is —O— or a single bond, M is a lactone ring or an acrylate group, and n stands for an integer of from 4 to 10.

12. An oriented film comprising the polymer of claim 11.

13. An optical component provided with a polymer as defined in claim 11 or an oriented film as defined in claim 12.

* * * * *